(12) United States Patent
Weinschenk et al.

(10) Patent No.: US 11,648,276 B2
(45) Date of Patent: *May 16, 2023

(54) IMMUNOTHERAPY AGAINST NEURONAL AND BRAIN TUMORS

(71) Applicant: Immatics Biotechnologies GmbH, Tuebingen (DE)

(72) Inventors: Toni Weinschenk, Aichwald (DE); Oliver Schoor, Tuebingen (DE); Claudia Trautwein, Wuelfrath (DE); Norbert Hilf, Kirchentellinsfurt (DE); Steffen Walter, Houston, TX (US); Harpreet Singh, Munich (DE)

(73) Assignee: IMMATICS BIOTECHNOLOGIES GMBH, Tuebingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/891,841

(22) Filed: Jun. 3, 2020

(65) Prior Publication Data
US 2020/0345777 A1    Nov. 5, 2020

Related U.S. Application Data

(60) Continuation of application No. 16/507,437, filed on Jul. 10, 2019, now Pat. No. 10,709,735, which is a
(Continued)

(30) Foreign Application Priority Data

Jul. 27, 2007  (EP) .................... 07014797
Mar. 27, 2008  (EP) .................... 08005889

(51) Int. Cl.
| | | |
|---|---|---|
| *C07K 7/06* | (2006.01) |
| *C07K 14/47* | (2006.01) |
| *C07K 14/495* | (2006.01) |
| *C07K 14/725* | (2006.01) |
| *A61K 35/17* | (2015.01) |
| *C07K 7/08* | (2006.01) |
| *A61K 39/00* | (2006.01) |
| *C07K 16/40* | (2006.01) |
| *C07K 19/00* | (2006.01) |
| *C12N 9/02* | (2006.01) |
| *C12N 9/10* | (2006.01) |

(Continued)

(52) U.S. Cl.
CPC .......... *A61K 35/17* (2013.01); *A61K 39/0011* (2013.01); *C07K 7/06* (2013.01); *C07K 7/08* (2013.01); *C07K 14/47* (2013.01); *C07K 14/4748* (2013.01); *C07K 14/495* (2013.01); *C07K 14/7051* (2013.01); *C07K 16/40* (2013.01); *C07K 19/00* (2013.01); *C12N 5/0638* (2013.01); *C12N 9/0036* (2013.01); *C12N 9/13* (2013.01); *A61K 38/00* (2013.01); *A61K 2039/5158* (2013.01); *A61K 2039/572* (2013.01); *C07K 2317/34* (2013.01); *C07K 2319/00* (2013.01); *C12N 2502/1157* (2013.01); *C12Y 208/02011* (2013.01)

(58) Field of Classification Search
CPC .... A61K 35/17; A61K 39/0011; A61K 38/00; A61K 2039/5158; A61K 2039/572; A61K 39/00; A61K 38/17; C07K 7/06; C07K 7/08; C07K 14/47; C07K 14/4748; C07K 14/495; C07K 14/7051; C07K 16/40; C07K 19/00; C07K 2317/34; C07K 2319/00; C07K 14/705; C07K 14/435; C12N 5/0638; C12N 9/0036; C12N 9/13; C12N 2502/1157; C12N 5/0636; C12N 5/10; C12N 15/63; C12Y 208/02011; A61P 37/02; A61P 37/04; A61P 35/00
See application file for complete search history.

(56) References Cited

U.S. PATENT DOCUMENTS 5,651,972 A   7/1997   Moyer et al.
6,747,137 B1  6/2004   Weinstock et al.
(Continued)

FOREIGN PATENT DOCUMENTS

EP   2111867    10/2009
EP   0900972    2/2010
(Continued)

OTHER PUBLICATIONS

Sikora et al., Pharmaceuticals, 2020, issue 13 p. 9 of 29, bullet 3.1 (Year: 2020).*
(Continued)

*Primary Examiner* — Stacey N Macfarlane
(74) *Attorney, Agent, or Firm* — McBee Moore & Vanik IP, LLC

(57) ABSTRACT

The present invention relates to peptides, nucleic acids and cells for use in immunotherapeutic methods. In particular, the present invention relates to the immunotherapy of cancer. The present invention furthermore relates to tumor-associated cytotoxic T cell (CTL) peptide epitopes, alone or in combination with other tumor-associated peptides that serve as active pharmaceutical ingredients of vaccine compositions that stimulate anti-tumor immune responses. The present invention relates to 11 novel peptide sequences and their variants derived from HLA class I and class II molecules of human tumor cells that can be used in vaccine compositions for eliciting anti-tumor immune responses.

20 Claims, 5 Drawing Sheets
Specification includes a Sequence Listing.

Related U.S. Application Data continuation of application No. 16/196,402, filed on Nov. 20, 2018, now Pat. No. 10,420,800, which is a continuation of application No. 14/865,278, filed on Sep. 25, 2015, now abandoned, which is a division of application No. 12/180,170, filed on Jul. 25, 2008, now Pat. No. 9,175,040.

(60) Provisional application No. 61/041,129, filed on Mar. 31, 2008, provisional application No. 60/953,161, filed on Jul. 31, 2007.

(51) Int. Cl.
*C12N 5/0783* (2010.01)
*A61K 38/00* (2006.01)

(56) References Cited

U.S. PATENT DOCUMENTS

| | | | |
|---|---|---|---|
| 9,175,040 B2 * | 11/2015 | Weinschenk | A61P 35/00 |
| 2002/0146370 A1 | 10/2002 | Mueller et al. | |
| 2003/0118585 A1 | 6/2003 | Mueller et al. | |
| 2010/0158929 A1 | 6/2010 | Lewandrowski et al. | |

FOREIGN PATENT DOCUMENTS

| | | |
|---|---|---|
| WO | 2000075339 | 12/2000 |
| WO | 2003042661 A2 | 5/2003 |
| WO | 2005071059 A2 | 8/2005 |
| WO | 20050071059 | 8/2005 |
| WO | 2005006051 A2 | 12/2005 |
| WO | 20050116051 | 12/2005 |
| WO | 2007028573 | 3/2007 |

OTHER PUBLICATIONS

Strioga et al., CD8+ CD28) and CD8+ CD57+ T cells and their role in health and disease, Immunology, 134:17-32, 2011.
Bel Yakov et al., "Activating CTL precursors to reveal function without skewing the repertoire by in vitro expansion" : =ur. J_ Immunol. (2001) vol. 31: 3557-3566.
Dutoit et al., Brain, 135; 1042-1054, 2012.
Meziere et al., J Immunol, 159(7):3230-3237, 1997.
Kallinteris et al., Expert Opin Biol Ther. 6(12):1311-1321, 2006.
Murphy, et al., Janeway's immunobiology, 7th Ed., Chapter 3, pp. 123-140 (Garland Sci., Nov. 27, 2007).
Rammensee et al., "SYFPEITHI: Database for MHC ligands and peptide motifs", Immunogenetics, (1999), vol. 50, pp. 213-219.
Trevino et al., "Measuring and Increasing Protein Solubility", Journal of Pharmaceutical Sciences, vol. 97, No. 10, Oct. 2008, pp. 4155-4166.
Colombetti et al., "Prolonged TCR/CD28 Engagement drives IL-2 Independent T Cell Clonal Expansion through signaling mediated by the Mammalian Target of Rapamycin", Journal of Immunology, vol. 176, Mar. 1, 2006, pp. 2730-2738.
Fong et al., "Altered peptide ligand vaccination with Flt3 ligand expanded dendritic cells for tumor immunotherapy", PNAS, Jul. 17, 2001, vol. 98, No. 15, pp. 8809-8814.
Zaremba et al., "Identification of an enhancer agonist cytotoxic T lymphocyte peptide from human carcinoembryonic antigen". Cancer Res., (1997), vol. 57, pp. 4570-4577.
Appay et al., "Decreased specific CD8+ T Cell cross-reactivity of antigen recognition following vaccination with Melan-A peptide", Eur. J. Immunology, May 4, 2006, vol. 36, pp. 1805-1814.
Strubin et al., "The complete sequence of the mRNA for the HLA-DR-associated invariant chain reveals a bolypeptide with an unusual transmembrane polarity", EMBO J, vol. 3, Issue 4, pp. 869-872 (Apr. 1984).
Gen Bank Accession No. X00497 (Feb. 10, 1999).
Paul J Mulholland et al.: "Genomic Profiling Identifies Discrete Deletions Associated With Franslocations in Glioblastoma Multiforme", Cell Cycle (Georgetown, Tex.) Apr. 2006, pp. 783-791; XP002484251 Cited in the Application; Abstract.
Database Uniprot [Online], Jun. 1, 2001, "Subname: Full=PTPRZL Protein; Flags: Fragment;" XP002484252, Retrieved From EBI Accession No. Uniprot: Q99LN6 Database Accession No. Q99LN6 Sequenc 100% Identical With Present Sequence 1.
Database Uniprot [Online], Nov. 1, 1991, "Recname: Full=Receptor-Typetyrosine-Protein Phosphatase Zeta; Short=R-Ptp-Zeta; Ec=<A Href="http://srs.eblac.uk/srsbin/cgi-bin/wgetz?[Enzyme-Ecnumber:3.1.3.48]+-E">3.1.3.48</A>; Altname: Full=R-Ptr-Zeta-2; Al Tname Full=Protein-Tyrosine Phosphatase Receptor Type Z Polypeptide 1; Al Tname: Full=Prot XP002502066, EBI Accession No. UNIPROT: P23471, Database Accession No. UNIPROT: P23471.
Search Report for PCT/EP2008/006154 dated Oct. 31, 2008.
Olson and Mc Neel, Expert Rev Vaccines, 11 (11 ): 1315-17, Nov. 2012.
Yu et al., Cancer Research 64: 4973-4979, Jul. 2004.
Plautz et al., Clinical Cancer Research, vol. 6, 2209-2218, Jun. 2000.

* cited by examiner

IMMUNOTHERAPY AGAINST NEURONAL AND BRAIN TUMORS

CROSS REFERENCE TO RELATED APPLICATIONS

This application is a continuation of U.S. application Ser. No. 16/507,437, filed 10 Jul. 2019, which is a continuation of U.S. application Ser. No. 16/196,402, filed Nov. 20, 2018 (now U.S. Pat. No. 10,420,800, issued Sep. 24, 2019), which is a continuation of U.S. application Ser. No. 14/865,278, filed Sep. 25, 2015, which is a division of U.S. application Ser. No. 12/180,170, filed Jul. 25, 2008 (now U.S. Pat. No. 9,175,040, issued Nov. 3, 2015), which claims priority to U.S. Provisional Application No. 61/041,129, filed Mar. 31, 2008, U.S. Provisional Application No. 60/953,161, filed Jul. 31, 2007, European Patent Application No. 08005889.4, filed Mar. 27, 2008, and European Patent Application No. 07014797.0, filed Jul. 27, 2007, the contents of which are incorporated herein by reference in their entireties.

REFERENCE TO SEQUENCE LISTING SUBMITTED AS A COMPLIANT ASCII TEXT FILE (.txt)

A Sequence Listing is submitted herewith as an ASCII compliant text file named "Sequence_Listing_2912919-017005_ST25.txt"), created on Jun. 2, 2020, and having a size of 2,262 bytes as permitted under 37 C.F.R. § 1.821 (c). The material in the aforementioned file is hereby incorporated by reference in its entirety.

BACKGROUND

Field of the Invention

The present invention relates to peptides, nucleic acids and cells for use in immunotherapeutic methods. In particular, the present invention relates to the immunotherapy of cancer. The present invention furthermore relates to tumor-associated cytotoxic T cell (CTL) peptide epitopes, alone or in combination with other tumor-associated peptides that serve as active pharmaceutical ingredients of vaccine compositions that stimulate anti-tumor immune responses. The present invention relates to 11 novel peptide sequences and their variants derived from HLA class I and class II molecules of human tumor cells that can be used in vaccine compositions for eliciting anti-tumor immune responses.

Description of Related Art

Gliomas are brain tumors originating from glial cells in the nervous system. Glial cells, commonly called neuroglia or simply glia, are non-neuronal cells that provide support and nutrition, maintain homeostasis, form myelin, and participate in signal transmission in the nervous system. The two most important subgroups of gliomas are astrocytomas and oligodendrogliomas, named according to the normal glial cell type from which they originate (astrocytes or oligodendrocytes, respectively). Belonging to the subgroup of astrocytomas, glioblastoma multiforme (referred to as glioblastoma hereinafter) is the most common malignant brain tumor in adults and accounts for approx. 40% of all malignant brain tumors and approx. 50% of gliomas (CBTRUS, 2006). It aggressively invades the central nervous system and is ranked at the highest malignancy level (grade IV) among all gliomas. Although there has been steady progress in their treatment due to improvements in neuroimaging, microsurgery, diverse treatment options such as temozolomide, and radiation, glioblastomas remain incurable (Macdonald, 2001; Burton and Prados, 2000; Prados and Levin, 2000). The lethal rate of this brain tumor is very high: the average life expectancy is 9 to 12 months after first diagnosis. The 5-year survival rate from 1986 to 1990 was 8.0%. To date, the five-year survival rate following aggressive therapy including gross tumor resection is still less than 10% (Burton and Prados, 2000; Nieder et al., 2000; Napolitano et al., 1999; Dazzi et al., 2000). Accordingly, there is a strong medical need for an alternative and effective therapeutic method.

Tumor cells of glioblastomas are the most undifferentiated ones among brain tumors, so the tumor cells have high potential of migration and proliferation and are highly invasive, leading to very poor prognosis. Glioblastomas lead to death due to rapid, aggressive, and infiltrative growth in the brain. The infiltrative growth pattern is responsible for the unresectable nature of these tumors. Glioblastomas are also relatively resistant to radiation and chemotherapy, and, therefore, post-treatment recurrence rates are high. In addition, the immune response to the neoplastic cells is rather ineffective in completely eradicating all neoplastic cells following resection and radiation therapy (Roth and Weller, 1999; Dix et al., 1999; Sablotzki et al., 2000).

Glioblastoma is classified into primary glioblastoma (de novo) and secondary glioblastoma, depending on differences in the gene mechanism during malignant transformation of undifferentiated astrocytes or glial precursor cells. Secondary glioblastoma occurs in a younger population of up to 45 years of age. During 4 to 5 years on average, secondary glioblastoma develops from lower-grade astrocytoma through undifferentiated astrocytoma. In contrast, primary glioblastoma predominantly occurs in an older population with a mean age of 55 years. Generally, primary glioblastoma occurs as fulminant glioblastoma characterized by tumor progression within 3 months from the state with no clinical or pathological abnormalities (Pathology and Genetics of the Nervous Systems. 29-39 (IARC Press, Lyon, France, 2000)).

Glioblastoma migrates along myelinated nerves and spreads widely in the central nervous system. In most cases surgical treatment shows only limited sustainable therapeutic effect (Neurol. Med. Chir. (Tokyo) 34, 91-94, 1994; Neurol. Med. Chir. (Tokyo) 33, 425-458, 1993; Neuropathology 17, 186-188, 1997) (Macdonald, 2001; Prados and Levin, 2000).

Malignant glioma cells evade detection by the host's immune system by producing immunosuppressive agents that impair T cell proliferation and production of the immune-stimulating cytokine IL-2 (Dix et al., 1999).

Intracranial neoplasms can arise from any of the structures or cell types present in the CNS, including the brain, meninges, pituitary gland, skull, and even residual embryonic tissue. The overall annual incidence of primary brain tumors in the United States is 14 cases per 100,000. The most common primary brain tumors are meningiomas, representing 27% of all primary brain tumors, and glioblastomas, representing 23% of all primary brain tumors (whereas glioblastomas account for 40% of malignant brain tumor in adults). Many of these tumors are aggressive and of high grade. Primary brain tumors are the most common solid tumors in children and the second most frequent cause of cancer death after leukemia in children.

The search for effective treatment of glioblastomas in patients is still ongoing today. Immunotherapy, or treatment via recruitment of the immune system, to fight these neoplastic cells has been investigated. First encouraging results were obtained in immuno-therapeutic studies in humans, in which antigen-specific CTL responses could be induced leading to prolonged median survival times compared to that obtained applying standard treatment accompanied by minimal toxicity (Heimberger et al., 2006).

There thus remains a need for a new efficacious and safe treatment option for brain tumors and to enhance the well-being of the patients without using chemotherapeutic agents or other agents that may lead to severe side effects. The present invention fulfils this need.

SUMMARY OF THE INVENTION

The present invention provides peptides comprising a sequence that is selected from the group consisting of SEQ ID NO: 1 to SEQ ID NO: 11 or a variant thereof which is 80% homologous to SEQ ID NO: 1 to SEQ ID NO: 11 or a variant, which will induce T cells cross-reacting with the peptide. Preferably the peptide maintains the ability to bind to a molecule of the human major histocompatibility complex (MHC) class-I or -II and wherein the peptide is capable of stimulating CD4 or CD8 T cells. In other embodiments, the peptide sequence is at least 80% homologous to the sequence set forth in SEQ D NO:1 to SEQ ID NO:11 and maintains the ability to bind to a molecule of the human major histocompatibility complex (MHC) class-I or -II, and wherein the peptide is capable of stimulating CD4 or CD8 T cells.

In a preferred embodiment the peptide comprises the amino acid sequence set forth in SEQ ID NO:1. The invention also provides a variant of this peptide wherein the variant binds to a MHC class I molecule HLA A*0205 allele and wherein the variant is capable of stimulating CD8 cells, and wherein the variant has the following motif $X_1$, $X_2$, $X_3$, $X_4$, $X_5$, $X_6$, $X_7$, $X_8$, $X_9$, wherein
$X_1$ is A, V, or Y;
$X_2$ is L;
$X_3$ is T, P, F, I or M;
$X_4$ is T, E, D, K, or N;
$X_5$ is L, V, L or I;
$X_6$ is M, I, V, L, I or A;
$X_7$ is H or V;
$X_8$ is Q or Y; and
$X_9$ is L.

In another preferred embodiment, the peptide comprises the amino acid sequence set forth in SEQ ID NO:2. The invention also provides a variant of this peptide wherein the variant binds to a MHC class I molecule HLA A*02 allele and wherein the variant is capable of stimulating CD8 cells, and wherein the variant has the following motif $X_1$, $X_2$, $X_3$, $X_4$, $X_5$, $X_6$, $X_7$, $X_8$, $X_9$,
wherein
$X_1$ is F, I, L, K, M, Y, or V;
$X_2$ is L or M;
$X_3$ is Y, A, F, P, M, S, or R;
$X_4$ is K, E, G, P, D, or T;
$X_5$ is V, I, K, Y, N, G, F, or H;
$X_6$ is I, L, or T;
$X_7$ is L, A, Y, or H;
$X_8$ is S, K, E, or S; and
$X_9$ is L.

In another embodiment, the peptide comprises the amino acid sequence set forth in SEQ ID NO:3. The invention also provides a variant of this peptide wherein the variant binds to a MHC class I molecule HLA A*02 allele and wherein the variant is capable of stimulating CD8 cells, and wherein the variant has the following motif $X_1$, $X_2$, $X_3$, $X_4$, $X_5$, $X_6$, $X_7$, $X_8$, $X_9$, wherein
$X_1$ is A, I, L, F, K, M, Y or V;
$X_2$ is I, M or L;
$X_3$ is I, A, Y, F, P, M, S or R;
$X_4$ is D, E, G, P or T;
$X_5$ is G, I, K, Y, N, F or V;
$X_6$ is V, I, L or T;
$X_7$ is E, A, Y or H;
$X_8$ is S, K, or E; and
$X_9$ is V or L.

The present invention further provides a peptide comprising the amino acid sequence set forth in SEQ ID NO:4. The invention also provides a variant of this peptide wherein the variant binds to a MHC class I molecule HLA A*02 allele and wherein the variant is capable of stimulating CD8 cells, and wherein the variant has the following motif $X_1$, $X_2$, $X_3$, $X_4$, $X_5$, $X_6$, $X_7$, $X_8$, $X_9$, wherein
$X_1$ is F, I, L, K, M, Y or V;
$X_2$ is L or M;
$X_3$ is L, A, Y, F, P, M, S or R;
$X_4$ is P, E, G, D, T or K;
$X_5$ is D, I, K, Y, N, G, F, V or H;
$X_6$ is T, I or L;
$X_7$ is D, A, Y or H;
$X_8$ is G, K, E or S; and
$X_9$ is L.

In another embodiment, the peptide comprises the amino acid sequence set forth in SEQ ID NO:5. The invention also provides a variant of this peptide of this peptide wherein the variant binds to a MHC class I molecule HLA A*02 allele and wherein the variant is capable of stimulating CD8 cells, and wherein the variant has the following motif $X_1$, $X_2$, $X_3$, $X_4$, $X_5$, $X_6$, $X_7$, $X_8$, $X_9$, wherein
$X_1$ is K, I, L, F, M or Y;
$X_2$ is V, M or L;
$X_3$ is F, A, Y, P, M or S;
$X_4$ is A, E, G, P or T;
$X_5$ is G, I, K, Y, N, F or V;
$X_6$ is I, L or T;
$X_7$ is P, A, Y or H;
$X_8$ is T, K, or E; and
$X_9$ is V or L.

In another embodiment, the peptide comprises the amino acid sequence set forth in SEQ ID NO:6. The invention also provides a variant of this peptide wherein the variant binds to a MHC class I molecule HLA A*02 allele and wherein the variant is capable of stimulating CD8 cells, and wherein the variant has the following motif $X_1$, $X_2$, $X_3$, $X_4$, $X_5$, $X_6$, $X_7$, $X_8$, $X_9$, wherein
$X_1$ is Q, V or Y;
$X_2$ is Q;
$X_3$ is S, P, F, I or M;
$X_4$ is D, E, K, N or P;
$X_5$ is Y, V, L or I;
$X_6$ is S, I, V, L or A;
$X_7$ is A, H or V;
$X_8$ is A or Y; and
$X_9$ is. L.

In another embodiment, the peptide comprises the amino acid sequence set forth in SEQ ID NO:7. The invention also provides a variant of this peptide wherein the variant binds to a MHC class I molecule HLA A*02 allele and wherein the variant is capable of stimulating CD8 cells, and wherein the variant has the following motif $X_1$, $X_2$, $X_3$, $X_4$, $X_5$, $X_6$, $X_7$, $X_8$, $X_9$, wherein $X_1$ is T, V or Y;
$X_2$ is Q;
$X_3$ is D, P, F, I or M;
$X_4$ is D, E, K, N or P;
$X_5$ is Y, V, L or I;
$X_6$ is V, I, L or A;
$X_7$ is L, H or V;
$X_8$ is E or Y; and
$X_9$ is V or L.

In another embodiment, the peptide comprises the amino acid sequence set forth in SEQ ID NO:8. The invention also provides a variant of this peptide wherein the variant binds to a MHC class I molecule HLA B*38 allele wherein the variant binds to a MHC class I molecule HLA B*38 allele and wherein the variant is capable of stimulating CD8 cells, and wherein the variant has the following motif $X_1$, $X_2$, $X_3$, $X_4$, $X_5$, $X_6$, $X_7$, $X_8$, $X_9$, wherein $X_1$ is Q or I;
$X_2$ is H;
$X_3$ is E or D;
$X_4$ is G, E, P, L, K or S;
$X_5$ is T, M, V, A, R, N or H;
$X_6$ is V, I, T or K;
$X_7$ is N, Y, V or N;
$X_8$ is I, K, Y, N or R; and
$X_9$ is F.

In certain embodiments the peptide has an overall length of between 8 and 100, preferably between 8 and 30, and most preferably between 8 and 16 amino acids. The peptide preferably has ability to bind to a molecule of the human major histocompatibility complex (MHC) class-I or -II.

In other embodiments, the peptide consists of or consists essentially of an amino acid sequence according to SEQ ID NO: 1 to SEQ ID NO: 11.

The peptides of the invention may be modified or includes non-peptide bonds. The peptides of the invention may be a fusion protein, in particular comprising N-terminal amino acids of the HLA-DR antigen-associated invariant chain (Ii).

The present invention also provides nucleic acids encoding the peptides of the invention. The nucleic acid may be DNA, cDNA, PNA, CNA, RNA or combinations thereof. The present invention also provides expression vectors capable of expressing the nucleic acids of the invention.

Peptides, nucleic acids or expression vectors of the invention may be used in medicine.

The present invention also provides a host cell host cell comprising a nucleic acid or an expression vector according to the invention. In preferred embodiments, the host cell is an antigen presenting cell, in particular a dendritic cell.

The present invention further provides a method of producing a peptide of the invention, the method comprising culturing a host cell of the invention and isolating the peptide from the host cell or its culture medium.

The present invention also provides an in vitro method for producing activated cytotoxic T lymphocytes (CTL), the method comprising contacting in vitro CTL with antigen loaded human class I or II MHC molecules expressed on the surface of a suitable antigen-presenting cell or an artificial construct mimicking an antigen-presenting cell for a period of time sufficient to activate the CTL in an antigen specific manner, wherein the antigen is a peptide according to the invention. In a preferred embodiment, the antigen is loaded onto class I or II MHC molecules expressed on the surface of a suitable antigen-presenting cell or an artificial construct mimicking an antigen-presenting cell by contacting a sufficient amount of the antigen with an antigen-presenting cell or an artificial construct mimicking an antigen-presenting cell or precursors thereof. Preferably, the antigen-presenting cell comprises an expression vector capable of expressing a peptide of the invention.

The present invention further provides activated cytotoxic T lymphocytes (CTL), produced by the methods described herein, which selectively recognise a cell aberrantly expressing a peptide of the invention.

The present invention also provides a method of killing target cells in a patient wherein the target cells aberrantly express a peptide of the present invention, the method comprising administering to the patient an effective number of cytotoxic T lymphocytes (CTL) of the invention.

The present invention also provides the use of any peptide, nucleic acid, expression vector, cell, or activated T lymphocyte of the invention as a medicament or in the manufacture of a medicament. Preferably the medicament is a vaccine and is active against cancer. The cancer may be, but is not limited to astrocytoma, pilocytic astrocytoma, dysembryoplastic neuroepithelial tumor, oligodendrogliomas, ependymoma, glioblastoma multiforme, mixed gliomas, oligoastrocytomas, medulloblastoma, retinoblastoma, neuroblastoma, germinoma, teratoma, gangliogliomas, gangliocytoma, central gangliocytoma, primitive neuroectodermal tumors (PNET, e.g. medulloblastoma, medulloepithelioma, neuroblastoma, retinoblastoma, ependymoblastoma), tumors of the pineal parenchyma (e.g. pineocytoma, pineoblastoma), ependymal cell tumors, choroid plexus tumors, neuroepithelial tumors of uncertain origin (e.g. gliomatosis cerebri, astroblastoma) or glioblastoma cells.

DETAILED DESCRIPTION OF THE INVENTION

Figure 1A:
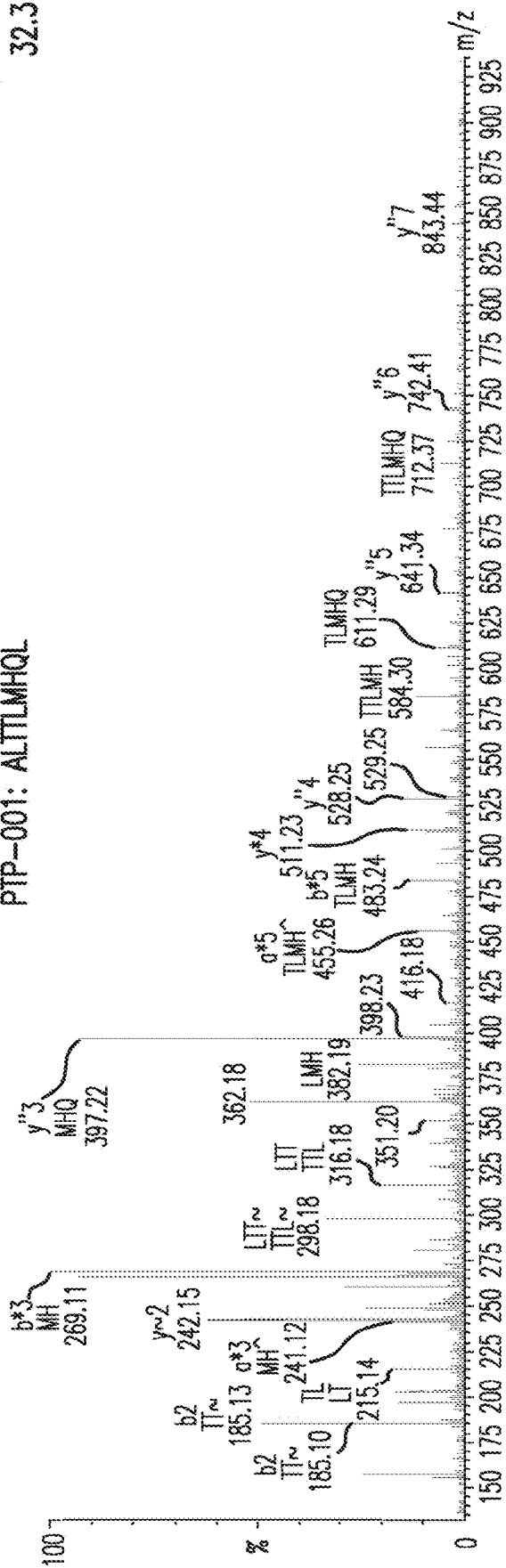
FIGS. 1A and 1B show the ESI-liquid chromatography mass spectra identifying tumor associated peptides (TUMAPs) PTP-001 from glioblastoma sample GB1006 and PTP-002 from glioblastoma sample GB6003 that were presented in a MHC class I restricted manner.

Stimulation of an immune response is dependent upon the presence of antigens recognized as foreign by the host immune system. The discovery of the existence of tumor associated antigens has now raised the possibility of using a host's immune system to foster an immune response that is specific for target antigens expressed on the surface of tumor cells, and through this mechanism of action is capable of inducing regression, stasis or slowed growth of the tumor. Various mechanisms of harnessing both the humoral and cellular arms of the immune system are currently being explored for cancer immunotherapy.

Specific elements of the cellular immune response are capable of specifically recognizing and destroying tumor cells. The isolation of cytotoxic T cells (CTL) from tumor-infiltrating cell populations or from peripheral blood suggests that such cells play an important role in natural immune defenses against cancer (Cheever et al., 1993; Zeh, III et al., 1999). Based on the analysis of 415 specimens from patients suffering from colorectal cancer, Galon et al. were able to demonstrate that type, density and location of immune cells in tumor tissue are actually a better predictor for survival of patients than the widely employed TNM-staging of tumors (Galon et al., 2006). CD8-positive T cells (TCD8+) in particular, which recognise Class I molecules of the major histocompatibility complex (MHC)-bearing peptides of usually 8 to 10 amino acid residues derived from proteins, or defective ribosomal products (DRIPs) (Schubert et al., 2000) play an important role in this response. Also, peptides stemming from spliced proteins were described in the literature. The MHC-molecules of the human are also designated as human leukocyte antigens (HLA).

There are two classes of MHC-molecules: MHC class I molecules and MHC class II molecules. MHC molecules are composed of a alpha heavy chain and beta-2-microglobulin (MHC class I receptors) or an alpha and a beta chain (MHC class II receptors), respectively. Their three-dimensional conformation results in a binding groove, which is used for non-covalent interaction with peptides. MHC class I molecules can be found on most cells having a nucleus. MHC class I present peptides that result from proteolytic cleavage of predominantly endogenous proteins, DRIPs and larger peptides. MHC class II molecules can be found predominantly on professional antigen presenting cells (APCs), and primarily present peptides of exogenous or transmembrane proteins that are taken up by APCs during the course of endocytosis, and are subsequently processed (Cresswell, 1994). Complexes of peptide and MHC class I molecules are recognized by CD8-positive cytotoxic T-lymphocytes bearing the appropriate TCR (T-cell receptor), whereas complexes of peptide and MHC class II molecules are recognized by CD4-positive-helper-T cells bearing the appropriate TCR. It is well known that the TCR, the peptide and the MHC are thereby present in a stoichiometric amount of 1:1:1.

CD4-positive helper T cells play an important role in inducing and sustaining effective responses by CD8-positive cytotoxic T cells (Wang and Livingstone, 2003; Sun and Bevan, 2003; Shedlock and Shen, 2003). For this reason the identification of CD4-positive T-cell epitopes derived from tumor associated antigens (TAA) is of great importance for the development of pharmaceutical products for triggering anti-tumor immune responses (Kobayashi et al., 2002; Qin et al., 2003; Gnjatic et al., 2003).

In the absence of inflammation, expression of MHC class II molecules is mainly restricted to cells of the immune system, especially professional antigen-presenting cells (APC), e.g., monocytes, monocyte-derived cells, macrophages, dendritic cells. In cancer patients, cells of the tumor have surprisingly been found to express MHC class II molecules (Dengjel et al., 2006).

It was shown in mammalian animal models, e.g., mice, that even in the absence of CTL effector cells (i.e., CD8-positive T lymphocytes), CD4-positive T cells are sufficient for inhibiting manifestation of tumors via inhibition of angiogenesis by secretion of interferon-gamma (IFNγ) (Qin and Blankenstein, 2000). Additionally, it was shown that CD4-positive T cells recognizing peptides from tumor-associated antigens presented by HLA class II molecules can counteract tumor progression via the induction of antibody (Ab) responses (Kennedy et al., 2003). In contrast to tumor-associated peptides binding to HLA class I molecules, only a small number of class II ligands of TAA have been described so far.

Since the constitutive expression of HLA class II molecules is usually limited to cells of the immune system (Mach et al., 1996), the possibility of isolating class II peptides directly from primary tumors was not considered possible. However, Dengjel et al. were recently successful in identifying a number of MHC Class II epitopes directly from tumors (WO2007028574, EP1760088 B1); (Dengjel et al., 2006).

For a peptide to trigger (elicit) a cellular immune response, it must bind to an MHC-molecule. This process is dependent on the allele of the MHC-molecule and specific polymorphisms of the amino acid sequence of the peptide. MHC-class-I-binding peptides are usually 8-10 amino acid residues in length and usually contain two conserved residues ("anchors") in their sequence that interact with the corresponding binding groove of the MHC-molecule. In this way each MHC allele has a "binding motif" determining which peptides can bind specifically to the binding groove (Rammensee et al., 1997).

In the MHC class I dependent immune reaction, peptides not only have to be able to bind to certain MHC class I molecules expressed by tumor cells, they also have to be recognized by T cells bearing specific T cell receptors (TCR).

The antigens that are recognized by the tumor specific cytotoxic T lymphocytes, that is, their epitopes, can be molecules derived from all protein classes, such as enzymes, receptors, transcription factors, etc., which are expressed and, as compared to unaltered cells of the same origin, up-regulated in cells of the respective tumor.

The current classification of tumor associated antigens comprises the following major groups (Novellino et al., 2005):

1. Cancer-testis antigens: The first TAAs ever identified that can be recognized by T cells (van der Bruggen et al., 1991) belong to this class, which was originally called cancer-testis (CT) antigens because of the expression of its members in histologically different human tumors and, among normal tissues, only in spermatocytes/spermatogonia of testis and, occasionally, in placenta. Since the cells of testis do not express class I and II HLA molecules, these antigens cannot be recognized by T cells in normal tissues and can therefore be considered as immunologically tumor-specific. Well-known examples for CT antigens are the MAGE family members or NY-ESO-1.

2. Differentiation antigens: These TAAs are shared between tumors and the normal tissue from which the tumor arose; most are found in melanomas and normal melanocytes. Many of these melanocyte lineage-related proteins are involved in the biosynthesis of melanin and are therefore not tumor specific but nevertheless are widely used for cancer immunotherapy. Examples include, but are not limited to, tyrosinase and Melan-A/MART-1 for melanoma or PSA for prostate cancer.

3. Overexpressed TAAs: Genes encoding widely expressed TAAs have been detected in histologically different types of tumors as well as in many normal tissues, generally with lower expression levels. It is possible that many of the epitopes processed and potentially presented by normal tissues are below the threshold level for T-cell recognition, while their overexpression in tumor cells can trigger an anticancer response by breaking previously established tolerance. Prominent examples for this class of TAAs are Her-2/neu, Survivin, Telomerase or WT1.

4. Tumor specific antigens: These unique TAAs arise from mutations of normal genes (such as β-catenin, CDK4, etc.). Some of these molecular changes are associated with neoplastic transformation and/or progression. Tumor specific antigens are generally able to induce strong immune responses without bearing the risk for autoimmune reactions against normal tissues. On the other hand, these TAAs are in most cases only relevant to the exact tumor on which they were identified and are usually not shared between many individual tumors.

5. TAAs arising from abnormal post-translational modifications: Such TAAs may arise from proteins that are neither specific nor overexpressed in tumors, but nevertheless become tumor associated by posttranslational processes primarily active in tumors. Examples for this class arise from altered glycosylation patterns leading to novel epitopes in tumors, such as MUC1, or events like protein splicing during degradation, which may or may not be tumor specific (Hanada et al., 2004; Vigneron et al., 2004).

6. Oncoviral proteins: These TAAs are viral proteins that may play a critical role in the oncogenic process and, because they are foreign (not of human origin), they can evoke a T-cell response. Examples of such proteins are the human papilloma type 16 virus proteins, E6 and E7, which are expressed in cervical carcinoma.

For proteins to be recognized by cytotoxic T-lymphocytes as tumor-specific or -associated antigens, and to be used in a therapy, particular prerequisites must be fulfilled. The antigen should be expressed mainly by tumor cells and not, or in comparably small amounts, by normal healthy tissues. It is furthermore desirable that the respective antigen is not only present in a type of tumor, but also in high concentrations (i.e. copy numbers of the respective peptide per cell). Tumor-specific and tumor-associated antigens are often derived from proteins directly involved in transformation of a normal cell to a tumor cell due to a function e.g. in cell cycle control or suppression of apoptosis. Additionally, also downstream targets of the proteins directly causative for a transformation may be upregulated und thus may be indirectly tumor-associated. Such indirectly tumor-associated antigens may also be targets of a vaccination approach (Singh-Jasuja et al., 2004). In both cases it is essential that epitopes are present in the amino acid sequence of the antigen, since such a peptide ("immunogenic peptide") that is derived from a tumor associated antigen should lead to an in vitro or in vivo T-cell-response.

Basically, any peptide able to bind a MHC molecule may function as a T-cell epitope. A prerequisite for the induction of an in vitro or in vivo T-cell-response is the presence of a T cell with a corresponding TCR and the absence of immunological tolerance for this particular epitope.

Therefore, TAAs are a starting point for the development of a tumor vaccine. The methods for identifying and characterizing the TAAs are based on the use of CTL that can be isolated from patients or healthy subjects, or they are based on the generation of differential transcription profiles or differential peptide expression patterns between tumors and normal tissues (Lemmel et al., 2004; Weinschenk et al., 2002).

However, the identification of genes over-expressed in tumor tissues or human tumor cell lines, or selectively expressed in such tissues or cell lines, does not provide precise information as to the use of the antigens transcribed from these genes in an immune therapy. This is because only an individual subpopulation of epitopes of these antigens are suitable for such an application since a T cell with a corresponding TCR has to be present and immunological tolerance for this particular epitope needs to be absent or minimal. It is therefore important to select only those peptides from over-expressed or selectively expressed proteins that are presented in connection with MHC molecules against which a functional T cell can be found. Such a functional T cell is defined as a T cell, which upon stimulation with a specific antigen, can be clonally expanded and is able to execute effector functions ("effector T cell"). Typical effector functions of T cells include the secretion of Interferon-gamma, perforin, and granzymes.

T-helper cells play an important role in orchestrating the effector function of CTLs in anti-tumor immunity. T-helper cell epitopes that trigger a T-helper cell response of the $T_{H1}$ type support effector functions of CD8-positive killer T cells, which include cytotoxic functions directed against tumor cells displaying tumor-associated peptide/MHC complexes on their cell surfaces. In this way tumor-associated T-helper cell peptide epitopes, alone or in combination with other tumor-associated peptides, can serve as active pharmaceutical ingredients of vaccine compositions that stimulate anti-tumor immune responses.

Since both types of response, CD8 and CD4 dependent, contribute jointly and synergistically to the anti-tumor effect, the identification and characterization of tumor-associated antigens recognized by either CD8+ CTLs (ligand: MHC class I molecule+ peptide epitope) or by CD4-positive T-helper cells (ligand: MHC class II molecule+ peptide epitope) is important in the development of tumor vaccines. It is therefore an object of the present invention, to provide novel amino acid sequences for peptides that are able to bind to MHC complexes of either class.

Accordingly, the present invention provides peptides that are useful in treating glioblastoma. These peptides were directly shown by mass spectrometry to be naturally presented by HLA molecules on primary human glioblastoma samples (see example 1 and FIGS. 1A and 1B). The source gene from which these peptides are derived—PTPRZ1— was shown to be highly overexpressed in glioblastoma compared with normal tissues (see example 2 and FIG. 2) demonstrating a high degree of tumor association of these peptides, i.e. these peptides are strongly presented on tumor tissue but not on normal tissues. HLA-bound peptides can be recognized by the immune system, specifically T lymphocytes/T cells. T cells can destroy the cells presenting the recognized HLA/peptide complex, e. g. glioblastoma tumor cells presenting the PTPRZ1-derived peptides. Several peptides of the present invention have been shown to be capable of stimulating T cell responses (see example 3 and FIGS. 3A-3D). Thus, the peptides are useful for generating an immune response in a patient by which tumor cells can be destroyed. An immune response in a patient can be induced by direct administration of the described peptides or suitable precursor substances (e.g. elongated peptides, proteins, or nucleic acids encoding these peptides) to the patient, ideally in combination with an agent enhancing the immunogenicity (i.e. an adjuvant). The immune response originating from such a therapeutic vaccination can be expected to be highly specific against tumor cells because the target peptides of the present invention are not presented on normal tissues, preventing the risk of undesired autoimmune reactions against normal cells in the patient.

The presence of claimed tumor associated peptides (TUMAPs) on tissue biopsies can assist a pathologist in diagnosis of cancer. Detection of certain TUMAPs by means of antibodies, mass spectrometry or other methods known in the art can tell the pathologist that the tissue is malignant or inflamed or generally diseased. Presence of groups of TUMAPs can enable classification or subclassification of diseased tissues.

The detection of TUMAPs on diseased tissue specimen can enable the decision about the benefit of therapies involving the immune system, especially if T lymphocytes are known or expected to be involved in the mechanism of action. Loss of MHC expression is a well described mechanism by which infected of malignant cells escape immunosurveillance. Thus, presence of TUMAPs shows that this mechanism is not exploited by the analyzed cells.

TUMAPs might be used to analyze lymphocyte responses against those TUMAPs such as T cell responses or antibody responses against the TUMAP or the TUMAP complexed to MHC molecules. These lymphocyte responses can be used as prognostic markers for decision on further therapy steps. These responses can also be used as surrogate markers in immunotherapy approaches aiming to induce lymphocyte responses by different means, e.g. vaccination of protein, nucleic acids, autologous materials, adoptive transfer of lymphocytes. In gene therapy settings, lymphocyte responses against TUMAPs can be considered in the assessment of side effects. Monitoring of lymphocyte responses might also be a valuable tool for follow-up examinations of transplantation therapies, e.g. for the detection of graft versus host and host versus graft diseases.

TUMAPs can be used to generate and develop specific antibodies against MHC/TUMAP complexes. These can be used for therapy, targeting toxins or radioactive substances to the diseased tissue. Another use of these antibodies can be targeting radionuclides to the diseased tissue for imaging purposes such as PET. This use can help to detect small metastases or to determine the size and precise localization of diseased tissues.

Table 1 shows the peptides according to the invention, their respective SEQ ID NO:, the HLA alleles to which the respective peptides bind, and the source proteins from which these peptides may arise.

TABLE 1

Peptides of the present invention

| SEQ ID NO | Peptide Code | Sequence | HLA Alleles | Source Protein(s) |
|---|---|---|---|---|
| 1 | PTP-001 | ALTTLMHQL | A*0205 | PTPRZ1 |
| 2 | PTP-002 | FLYKVILSL | A*02 | PTPRZ1 |
| 3 | PTP-003 | AIIDGVESV | A*02 | PTPRZ1 |
| 4 | PTP-004 | FLLPDTDGL | A*02 | PTPRZ1 |
| 5 | PTP-005 | KVFAGIPTV | A*02 | PTPRZ1 |
| 6 | PTP-006 | QQSDYSAAL | A*02# | PTPRZ1 |
| 7 | PTP-007 | TQDDYVLEV | A*02# | PTPRZ1, PTPRG |
| 8 | PTP-008 | QHEGTVNIF | B*38 | PTPRZ1 |
| 9 | PTP-009 | SVFGDDNKALSK | not determined | PTPRZ1 |
| 10 | PTP-010 | EIGWSYTGALNQKN | HLA-DR | PTPRZ1 |
| 11 | CHI-001 | SLWAGVVVL | A*02 | CHI3L2 | probably subtype A*205

Surprisingly, PTP-002, SEQ ID NO:2 was also found to be presented in primary adenosquamous carcinoma (a form of lung cancer) and can therefore also be used for treating this type of cancer.

Protein Tyrosine Phosphatase, Receptor-Type, Zeta1 (PTPRZ1, PTP-ξ)

PTPRZ1 is a member of the receptor type protein tyrosine phosphatase family and encodes a single-pass type I membrane protein with two cytoplasmic tyrosine-protein phosphatase domains, an alpha-carbonic anhydrase domain and a fibronectin type-III domain (Wu et al., 2006), in breast cancer (Perez-Pinera et al., 2007), in the remyelinating oligodendrocytes of multiple sclerosis lesions (Harroch et al., 2002), and in human embryonic kidney cells under hypoxic conditions (Wang et al., 2005).

Both the protein and transcript are overexpressed in glioblastoma cells, promoting their haptotactic migration (Lu et al., 2005). Furthermore, PTRPZ1 is frequently amplified at the genomic DNA level in glioblastoma (Mulholland et al., 2006).

Kaplan et al. cloned 3 human receptor PTP genes, including PTP-γ (Kaplan et al., 1990). It was shown that one PTPG allele was lost in 3 of 5 renal carcinoma cell lines and in 5 of 10 lung carcinoma tumor samples tested. PTP-γ mRNA was expressed in kidney cell lines and lung cell lines but not in several hematopoietic cell lines tested. Thus, the PTP-γ gene appeared to have characteristics suggesting that it may be a tumor suppressor gene in renal and lung carcinoma. Gebbink et al. isolated a mouse cDNA of 5.7 kb, encoding a 'new' member of the family of receptor-like protein-tyrosine phosphatases, termed RPTPμ (Gebbink et al., 1991). The cDNA predicted a protein of 1,432 amino acids (not including the signal peptide) with a calculated molecular mass of 161,636 Da. In addition, they cloned the human homolog, which showed 98.7% amino acid homology to the mouse protein. The predicted mouse protein consisted of a 722-amino acid extracellular region, containing 13 potential N-glycosylation sites, a single transmembrane domain, and a 688-amino acid intracellular part containing two tandem repeats homologous to the catalytic domains of other tyrosine phosphatases. RNA blot analysis showed a single transcript that was most abundant in lung but present in much lower amounts in brain and heart as well. The human PTP gene was assigned to 18pter-q11 by Southern analysis of human/rodent somatic cell hybrid clones.

PTP-ε cDNA was isolated by Krueger et al. (Krueger et al., 1990). The 700-amino acid protein has a short extracellular domain and two tandemly repeated intracellular PTPase domains. High levels of PTP-e transcription were noted in the mouse brain and testes. Both isoforms of PTP-ε—transmembrane, receptor-type isoform and a shorter, cytoplasmic isoform—appear to arise from a single gene through the use of alternative promoters and 5-prime exons.

Barnea et al. (Barnea et al., 1993) cloned cDNAs for the human and mouse PTP-γ gene (designated PTP-γ by that group) from brain cDNA libraries, and analyzed their predicted polypeptide sequences. The human (1,445-amino acid) and mouse (1,442-amino acid) sequences share 95% identity at the amino acid level and predict a putative extracellular domain, a single transmembrane domain, and a cytoplasmic region with 2 tandem catalytic tyrosine phosphatase domains. The extracellular domain contains a stretch of 266 amino acids that are highly similar to the zinc-containing enzyme carbonic anhydrase (MIM 114800), suggesting that PTP-γ and PTP-ξ (PTPRZ1) represent a subfamily of 25 receptor tyrosine phosphatases. The gene for PTP-γ has 30 exons and is approximately 780 kb in size. It is much larger than the other receptor PTP genes, with the CD45 gene (MIM 151460) around 100 kb and the others even smaller.

Another receptor-type tyrosine phosphatase, protein tyrosine phosphatase zeta (PTPRZ1) [also known as PTP-ξ, HPTP-ZETA, HPTPZ, RPTP-BETA(β), or RPTPB] was isolated as a cDNA sequence by two groups in the early nineties. Levy et al. (Levy et al., 1993) isolated cDNA clones from a human infant brainstem mRNA expression library, and deduced the complete amino acid sequence of a large receptor-type protein tyrosine phosphatase containing 2,307 amino acids.

Levy found that the protein, which they designated PTPβ (PTPRZ1), is a transmembrane protein with 2 cytoplasmic PTPase domains and a 1,616-amino acid extracellular domain. As in PTP-γ (MIM 176886), the 266 N-terminal residues of the extracellular domain have a high degree of similarity to carbonic anhydrases (see MIM 114880). The human gene encoding PTPRZ1 has been mapped to chromosome 7q31.3-q32 by chromosomal in situ hybridization (Ariyama et al., 1995). Northern blot analysis has shown that showed that PTP-zeta is expressed only in the human central nervous system. By in situ hybridization, (Levy et al., 1993) localized the expression to different regions of the adult human brain, including the Purkinje cell layer of the cerebellum, the dentate gyms, and the subependymal layer of the anterior horn of the lateral ventricle. Levy stated that this was the first mammalian tyrosine phosphatase whose expression is restricted to the nervous system. In addition, high levels of expression in the murine embryonic brain suggested an important role in CNS development.

Thus, the PTP receptor family of proteins has been characterized as a fairly diverse family of membrane-bound receptors, and non-membrane bound isoforms, which share a common PTPase cytosol domain architecture. Although their expression in fetal and embryonic tissues has suggested a developmental biology role for the proteins, their full function in normal and disease state biology is still not fully understood.

U.S. Pat. No. 6,455,026 identified PTP-ξ (PTPRZ1) as a target in the treatment and visualization of brain tumors. The application provided methods and reagents for specifically targeting brain tumor cells for both therapeutic and imaging purposes. PTP-ξ affinity-based compounds and compositions useful in treating a brain tumor in a patient were provided, whereas the compositions and compounds generally fell into two groups: PTP-ξ-binding conjugate compounds, which comprise a cytotoxic moiety, which inhibits the growth of tumor cells; and PTP-ξ-binding compound compositions in which the PTP-ξ binding moiety alters the normal function of PTP-ξ in the tumor cell, thus inhibiting cell growth.

In a first group, PTP ξ-binding therapeutic conjugate compounds were provided. These compounds had the general formula $\alpha(P_z)C$, wherein $\alpha(P_z)$ were one or more moieties that specifically bound to a human protein tyrosine phosphatase-ξ, and C was one or more cytotoxic moieties. In preferred embodiments (which was disclosed for all groups) $\alpha(P_z)$ was disclosed to be an antibody or an antibody fragment. In a second group, PTP-ξ-binding therapeutic compounds were provided that altered the normal function of PTP-ξ in brain tumor cells and inhibited brain tumor cell growth. These PTPRZ1-binding therapeutic compounds had the general formula $\alpha(P_z)$ wherein $\alpha(P_z)$ were one or more moieties that specifically bound to a human protein tyrosine phosphatase-ξ, and wherein the binding of $\alpha(P_z)$ altered the function of protein tyrosine phosphatase-ξ.

U.S. Pat. No. 7,060,275 B2 discloses splicing variants of PTPRZ1, vectors including these variants and antigens against various variants.

Chitinase 3-Like 2 (CHI3L2)

CHI3L2 was originally identified from chondrocytes. It has been frequently described as a target antigen in rheumatoid arthritis. No relevant association of CHI3L2 with cancer was identified. Chitinase 3-like proteins have been implied in stimulating proliferation of human connective tissue cells, e.g. fibroblasts, by activating extracellular signal-regulated kinase and PKB mediated signalling pathways (Recklies A D, et al., 2002). In mice, chitinase 3-like proteins have been found to be strongly upregulated in *Helicobacter*-induced gastric cancer models (Takaishi S, et al., 2007).

Nowhere in the prior art has the use of MHC-binding peptides derived from PTPRZ1 or CHI2L2 as active pharmaceutical ingredients for the treatment of brain tumors been considered.

Accordingly, in a first aspect, the invention provides a peptide comprising a sequence that is selected from the group of SEQ ID NO: 1 to SEQ ID NO: 11 or a variant thereof that is 80% homologous to SEQ ID NO: 1 to SEQ ID NO: 11 or a variant that will induce T cells cross-reacting with the peptide.

The peptides of the invention have the ability to bind to a molecule of the human major histocompatibility complex (MHC) class-I or -II.

In the present invention, the term "homologous" refers to the degree of identity between sequences of two amino acid sequences, i.e. peptide or polypeptide sequences. The aforementioned "homology" is determined by comparing two sequences aligned under optimal conditions over the sequences to be compared. The sequences to be compared may have an addition or deletion (for example, gap and the like) in the optimum alignment of the two sequences. Such a sequence homology can be calculated by creating an alignment using, for example, the ClustalW algorithm (Nucleic Acid Res., 22(22): 4673 4680 (1994). Commonly available sequence analysis software, more specifically, Vector NTI, GENETYX or analysis tools provided by public databases may be used for sequence alignment.

A person skilled in the art will be able to assess whether T cells induced by a variant of a specific peptide can cross-react with the peptide itself (Fong et al., 2001b); (Zaremba et al., 1997; Colombetti et al., 2006; Appay et al., 2006).

By a "variant" of the given amino acid sequence the inventors mean that the side chains of, for example, one or two of the amino acid residues are altered (for example by replacing them with the side chain of another naturally occurring amino acid residue or some other side chain) so that the peptide is still able to bind to an HLA molecule in substantially the same way as a peptide consisting of the given amino acid sequence in SEQ ID NO:1-11. For example, a peptide may be modified so that it at least maintains, if not improves, the ability to interact with, and bind to the binding groove of, a suitable MHC molecule, such as HLA-A*02 or -DR, and in that way it at least maintains, if not improves, the ability to bind to the TCR of activated CTL. These CTL can subsequently cross-react with cells and kill cells that express a polypeptide containing the natural amino acid sequence of the cognate peptide as defined in the aspects of the invention. As can be derived from the scientific literature (Rammensee et al., 1997) and databases (Rammensee et al., 1999), certain positions of HLA binding peptides are typically anchor residues forming a core sequence fitting to the binding motif of the HLA receptor, which is defined by polar, electrophysical, hydrophobic and spatial properties of the polypeptide chains constituting the binding groove. Thus one skilled in the art would be able to modify the amino acid sequences set forth in SEQ ID NO:1-11, by maintaining the known anchor residues, and would be able to determine whether such variants maintain the ability to bind MHC class I or II molecules. The variants of the present invention retain the ability to bind to the TCR of activated CTL, which can subsequently cross-react with- and kill cells that express a polypeptide containing the natural amino acid sequence of the cognate peptide as defined in the aspects of the invention.

Those amino acid residues that do not substantially contribute to interactions with the T-cell receptor can be modified by replacement with another amino acid whose incorporation does not substantially affect T-cell reactivity and does not eliminate binding to the relevant MHC. Thus, apart from the proviso given, the peptide of the invention may be any peptide (by which term the inventors include oligopeptide or polypeptide) that includes the amino acid sequences or a portion or variant thereof as given.

TABLE 2

Variants and motif of the peptides according to SEQ ID NO: 1 to 11

| | | Position | 1 | 2 | 3 | 4 | 5 | 6 | 7 | 8 | 9 |
|---|---|---|---|---|---|---|---|---|---|---|---|
| PTP-001 | Peptide Code Variants | | A | L | T | T | L | M | H | Q | L |
| | | | V | V | P | E | V | I | H | Y | |
| | | | Y | I | F | D | L | V | V | | |
| | | | | M | I | K | I | L | | | |
| | | | | | M | N | | A | | | |
| | | | | | | P | | | | | |
| | | Position | 1 | 2 | 3 | 4 | 5 | 6 | 7 | 8 | 9 |
| PTP-002 | Peptide Code Variants | | F | L | Y | K | V | I | L | S | L |
| | | | | M | | | | | | | |
| | | | | | | E | | | | K | |
| | | | I | | A | G | I | I | A | E | |
| | | | L | | Y | P | K | L | Y | S | |
| | | | F | | F | D | Y | T | H | | |
| | | | K | | P | T | N | | | | |
| | | | M | | M | | F | | | | |
| | | | Y | | S | | V | | | | |
| | | | V | | R | | | | | | |
| | | | | | | K | H | | | | |
| PTP-003 | Peptide Code Variants | Position | 1 | 2 | 3 | 4 | 5 | 6 | 7 | 8 | 9 |
| | | | A | I | I | D | G | V | E | S | V |
| | | | | M | | | | | | | L |
| | | | | L | | | | | | | L |
| | | | | | | E | | | | K | |
| | | | I | | A | G | I | I | A | E | |
| | | | L | | Y | P | K | L | Y | | |
| | | | F | | F | T | Y | T | H | | |
| | | | K | | P | | N | | | | |
| | | | M | | M | | F | | | | |
| | | | Y | | S | | V | | | | |
| | | | V | | R | | | | | | |
| PTP-004 | Peptide Code Variants | Position | 1 | 2 | 3 | 4 | 5 | 6 | 7 | 8 | 9 |
| | | | F | L | L | P | D | T | D | G | L |
| | | | | M | | | | | | | L |
| | | | | | | E | | | | K | |
| | | | I | | A | G | I | I | A | E | |
| | | | L | | Y | D | K | L | Y | S | |
| | | | K | | F | T | Y | | H | | |
| | | | M | | P | | N | | | | |
| | | | Y | | M | | G | | | | |
| | | | V | | S | | F | | | | |
| | | | | | R | | V | | | | |
| | | | | | | K | H | | | | |
| PTP-005 | Peptide Code Variants | Position | 1 | 2 | 3 | 4 | 5 | 6 | 7 | 8 | 9 |
| | | | K | V | F | A | G | I | P | T | V |
| | | | | M | | | | | | | L |
| | | | | L | | | | | | | L |
| | | | | | | E | | | | K | |
| | | | I | | A | G | I | | A | E | |
| | | | L | | Y | P | K | L | Y | | |
| | | | F | | P | T | Y | T | H | | |
| | | | M | | M | | N | | | | |
| | | | Y | | S | | F | | | | |
| | | | | | | | V | | | | |
| PTP-006 | Peptide Code Variants | Position | 1 | 2 | 3 | 4 | 5 | 6 | 7 | 8 | 9 |
| | | | Q | Q | S | D | Y | S | A | A | L |
| | | | V | | P | E | V | I | H | Y | |
| | | | Y | | F | K | L | V | V | | |
| | | | | | I | N | I | L | | | |
| | | | | | M | P | | A | | | |
| PTP-007 | Peptide Code Variants | Position | 1 | 2 | 3 | 4 | 5 | 6 | 7 | 8 | 9 |
| | | | T | Q | D | D | Y | V | L | E | V |
| | | | V | | P | E | V | I | H | Y | L |
| | | | Y | | F | K | L | V | V | | |
| | | | | | I | N | I | L | | | |
| | | | | | M | P | | A | | | |
| PTP-008 | Peptide Code Variants | Position | 1 | 2 | 3 | 4 | 5 | 6 | 7 | 8 | 9 |
| | | | Q | H | E | G | T | V | N | I | F |
| | | | I | | D | | | | | | |
| | | | | | | E | M | V | Y | K | |
| | | | | | | P | V | I | V | Y | |
| | | | | | | L | A | T | N | N | |
| | | | | | | E | R | | K | R | |
| | | | | | | G | N | | | | |
| | | | | | | L | H | | | | |
| | | | | | | K | | | | | |
| | | | | | | S | | | | | |

TABLE 2-continued

Variants and motif of the peptides according to SEQ ID NO: 1 to 11

| CHI-001 | Position | 1 | 2 | 3 | 4 | 5 | 6 | 7 | 8 | 9 |
|---|---|---|---|---|---|---|---|---|---|---|
| | Peptide Code Variants | S | L | W | A | G | V | V | V | L |
| | | | M | E | | | | | | K |
| | | I | | A | G | I | I | A | E | |
| | | L | | Y | P | K | L | Y | S | |
| | | F | | F | D | Y | T | H | | |
| | | K | | P | T | N | | | | |
| | | M | | M | | | | | | |
| | | Y | | S | | | F | | | |
| | | V | | R | | | V | | | |
| | | | | K | | | H | | | |

It is furthermore known for MHC-class II presented peptides that these peptides are composed of a "core sequence" having a amino acid sequence fitting to a certain HLA-allele-specific motif and, optionally, N- and/or C-terminal extensions that do not interfere with the function of the core sequence (i.e. are deemed as irrelevant for the interaction of the peptide and all or a subset of T cell clones recognising the natural counterpart). The N- and/or C-terminal extensions can, for example, be between 1 to 10 amino acids in length, respectively. These peptides can be used either directly to load MHC class II molecules or the sequence can be cloned into the vectors according to the description herein below. As these peptides constitute the final product of the processing of larger peptides within the cell, longer peptides can be used as well. The peptides of the invention may be of any size, but typically they may be less than 100,000 in molecular weight, preferably less than 50,000, more preferably less than 10,000 and typically about 5,000. In terms of the number of amino acid residues, the peptides of the invention may have fewer than 1,000 residues, preferably fewer than 500 residues, more preferably fewer than 100, more preferably fewer than 100 and most preferably between 30 and 8 residues. Accordingly, the present invention also provides peptides and variants thereof wherein the peptide or variant has an overall length of between 8 and 100, preferably between 8 and 30, and most preferred between 8 and 16, namely 8, 9, 10, 11, 12, 13, 14, 15, or 16 amino acids.

Correspondingly, naturally occurring or artificial variants that induce T cells cross-reacting with a peptide of the invention are often length variants. Examples for such naturally occurring length variants are given in Table 1 for SEQ ID NO: 11.

If a peptide that is longer than around 12 amino acid residues is used directly to bind to a MHC class II molecule, it is preferred that the residues flanking the core HLA binding region do not substantially affect the ability of the peptide to bind specifically to the binding groove of the MHC class II molecule or to present the peptide to the T (-helper) cell. However, as already indicated above, it will be appreciated that larger peptides may be used, e.g. when encoded by a polynucleotide, since these larger peptides may be fragmented by suitable antigen-presenting cells.

It is also possible, that MHC class I epitopes, although usually between 8-10 amino acids long, are generated by peptide processing from longer peptides or proteins that include the actual epitope. It is preferred that the residues flanking the actual epitope do not substantially affect proteolytic cleavage necessary to expose the actual epitope during processing.

Accordingly, the present invention also provides peptides and variants of MHC class I epitopes wherein the peptide or variant has an overall length of between 8 and 100, preferably between 8 and 30, and most preferred between 8 and 16, namely 8, 9, 10, 11, 12, 13, 14, 15, or 16 amino acids.

Of course, the peptide or variant according to the present invention will have the ability to bind to a molecule of the human major histocompatibility complex (MHC) class I or II. Binding of a peptide or a variant to a MHC complex may be tested by methods known in the art, for example those described in the literature for different MHC class II alleles (e.g., Vogt et al., 1994; Malcherek et al., 1994; Manici et al., 1999; Hammer et al., 1995; Tompkins et al., 1993; Boyton et al., 1998).

In a particularly preferred embodiment of the invention the peptide consists or consists essentially of an amino acid sequence according to SEQ ID NO: 1 to SEQ ID NO: 11.

"Consisting essentially of" shall mean that a peptide according to the present invention, in addition to the sequence according to any of SEQ ID NO: 1 to SEQ ID NO: 11 or a variant thereof, contains additional N- and/or C-terminally located stretches of amino acids do not necessarily form part of the peptide that functions as an epitope for MHC molecule epitope.

Nevertheless, these stretches can be important to provide an efficient introduction of the peptide according to the present invention into the cells. Accordingly, in one embodiment of the present invention, the peptide is a fusion protein that comprises, for example, the 80 N-terminal amino acids of the HLA-DR antigen-associated invariant chain (p33, in the following "Ii") as derived from the NCBI, GenBank Accession-number X00497 (Strubin, M. et al. 1984).

Examples of preferred peptides having a specific HLA-subtype and capable of stimulating CD8 cells, are peptides that comprise the specific anchor amino acid-motif as depicted in the following table 2a:

TABLE 2a

HLA-subtypes and anchor motifs of preferred peptides

| Peptide | HLA-subtype | | Position | 1 | 2 | 3 | 4 | 5 | 6 | 7 | 8 | 9 |
|---|---|---|---|---|---|---|---|---|---|---|---|---|
| 1 | A*0205 | Peptide Code | | A | L | T | T | L | M | H | Q | L |
| | | Anchor motif | | x | L | x | x | x | x | x | x | L |
| 2 | A*02 | Peptide Code | | F | L | Y | K | V | I | L | S | L |
| | | Anchor motif | | x | L | x | x | x | x | x | x | L |
| 3 | A*02 | Peptide Code | | A | I | I | D | G | V | E | S | V |
| | | Anchor motif | | x | I | x | x | x | x | x | x | V |
| 4 | A*02 | Peptide Code | | F | L | L | P | D | T | D | G | L |
| | | Anchor motif | | x | L | x | x | x | x | x | x | L |
| 5 | A*02 | Peptide Code | | K | V | F | A | G | I | P | T | V |
| | | Anchor motif | | x | V | x | x | x | x | x | x | V |

TABLE 2a-continued

HLA-subtypes and anchor motifs of preferred peptides

| Peptide | HLA-subtype | | Position | 1 | 2 | 3 | 4 | 5 | 6 | 7 | 8 | 9 |
|---|---|---|---|---|---|---|---|---|---|---|---|---|
| 6 | A*02 (probably subtype A*205) | Peptide Code | | Q | Q | S | D | Y | S | A | A | L |
| | | Anchor motif | | x | Q | x | x | x | x | x | x | L |
| 7 | A*02 (probably subtype A*205) | Peptide Code | | T | Q | D | D | Y | V | L | E | V |
| | | Anchor motif | | x | Q | x | x | x | x | x | x | V |
| 8 | B*38 | Peptide Code | | Q | H | E | G | T | V | N | I | F |
| | | Anchor motif | | x | H | E | x | x | x | x | x | F |
| 11 | A*02 | Peptide Code | | S | L | W | A | G | V | V | V | L |
| | | | | x | L | x | x | x | x | x | x | L |
| X | A*02 | General anchor motif for peptides | | x | L/I/V | x | x | x | x | x | x | L/V |

In addition, the peptide or variant may be modified further to improve stability and/or binding to MHC molecules to elicit a stronger immune response. Methods for these types of optimisation of a peptide sequence are well known in the art and include, for example, the introduction of reverse peptide bonds or non-peptide bonds.

In a reverse peptide, bond amino acid residues are not joined by peptide (—CO—NH—) linkages, but rather the peptide bond is reversed. Such retro-inverso peptidomimetics may be made using methods known in the art, for example such as those described in Meziere et al. (1997) J. Immunol. 159, 3230-3237, incorporated herein by reference. This approach involves making pseudopeptides containing changes involving the backbone, and not the orientation of side chains. Meziere et al. (1997) show that for MHC binding and T helper cell responses, these pseudopeptides are useful. Retro-inverse peptides, containing NH—CO bonds instead of CO—NH peptide bonds are much more resistant to proteolysis.

A non-peptide bond is, for example, —CH$_2$—NH, —CH$_2$S—, —CH$_2$CH$_2$—, —CH═CH—, —COCH$_2$—, —CH(OH)CH$_2$—, and —CH$_2$SO—. U.S. Pat. No. 4,897,445 provides a method for the solid phase synthesis of non-peptide bonds (—CH$_2$—NH) in polypeptide chains that involves polypeptides synthesised by standard procedures and the non-peptide bond synthesised by reacting an amino aldehyde and an amino acid in the presence of NaCNBH$_3$.

Peptides comprising the sequences described above may be synthesized with additional chemical groups present at their amino and/or carboxy termini, to enhance, for example, the stability, bioavailability, and/or affinity of the peptides. For example, hydrophobic groups such as carbobenzoxyl, dansyl, or t-butyloxycarbonyl groups may be added to the peptides' amino termini. Likewise, an acetyl group or a 9-fluorenylmethoxy-carbonyl group may be placed at the peptides' amino termini. Additionally, the hydrophobic group, t-butyloxycarbonyl, or an amido group may be added to the peptides' carboxy termini.

Further, the peptides of the invention may be synthesized to alter their steric configuration. For example, the D-isomer of one or more of the amino acid residues of the peptide may be used, rather than the usual L-isomer. Still further, at least one of the amino acid residues of the peptides of the invention may be substituted by one of the well known non-naturally occurring amino acid residues. Alterations such as these may serve to increase the stability, bioavailability and/or binding action of the peptides of the invention.

Similarly, a peptide or variant of the invention may be modified chemically by reacting specific amino acids either before or after synthesis of the peptide. Examples for such modifications are well known in the art and are summarized e.g. in R. Lundblad, Chemical Reagents for Protein Modification, 3rd ed. CRC Press, 2005, which is incorporated herein by reference. Chemical modification of amino acids includes, but is not limited to, modification by acylation, amidination, pyridoxylation of lysine, reductive alkylation, trinitrobenzylation of amino groups with 2, 4, 6-trinitrobenzene sulphonic acid (TNBS), amide modification of carboxyl groups and sulphydryl modification by performic acid oxidation of cysteine to cysteic acid, formation of mercurial derivatives, formation of mixed disulphides with other thiol compounds, reaction with maleimide, carboxymethylation with iodoacetic acid or iodoacetamide and carbamoylation with cyanate at alkaline pH, although without limitation thereto. In this regard, the skilled person is referred to Chapter 15 of Current Protocols In Protein Science, Eds. Coligan et al. (John Wiley & Sons NY 1995-2000) for more extensive methodology relating to chemical modification of proteins.

Briefly, modification of e.g. arginyl residues in proteins is often based on the reaction of vicinal dicarbonyl compounds such as phenylglyoxal, 2,3-butanedione, and 1,2-cyclohexanedione to form an adduct. Another example is the reaction of methylglyoxal with arginine residues. Cysteine can be modified without concomitant modification of other nucleophilic sites such as lysine and histidine. As a result, a large number of reagents are available for the modification of cysteine. The websites of companies such as Sigma-Aldrich provide information on specific reagents.

Selective reduction of disulfide bonds in proteins is also common. Disulfide bonds can be formed and oxidized during the heat treatment of biopharmaceuticals. Woodward's Reagent K may be used to modify specific glutamic acid residues. N-(3-(dimethylamino)propyl)-N'-ethylcarbodiimide can be used to form intra-molecular crosslinks between a lysine residue and a glutamic acid residue. Diethylpyrocarbonate is a reagent for the modification of histidyl residues in proteins. Histidine can also be modified using 4-hydroxy-2-nonenal. The reaction of lysine residues and other α-amino groups is, for example, useful in binding of peptides to surfaces or the cross-linking of proteins/ peptides. Lysine is the site of attachment of poly(ethylene) glycol and the major site of modification in the glycation of proteins. Methionine residues in proteins can be modified with e.g. iodoacetamide, bromoethylamine, chloramine T. Tetranitromethane and N-acetylimidazole can be used for the modification of tyrosyl residues. Cross-linking via the formation of dityrosine can be accomplished with hydrogen peroxide/copper ions. Recent studies on the modification of tryptophan have used N-bromosuccinimide, 2-hydroxy-5-nitrobenzyl bromide or 3-bromo-3-methyl-2-(2-nitrophenyl-mercapto)-3H-indole (BPNS-skatole).

Successful modification of therapeutic proteins and peptides with PEG is often associated with an extension of circulatory half-life, while cross-linking of proteins with glutaraldehyde, polyethyleneglycol diacrylate and formaldehyde is used for the preparation of hydrogels. Chemical modification of allergens for immunotherapy is often achieved by carbamylation with potassium cyanate.

A peptide or variant, wherein the peptide is modified or includes non-peptide bonds is a preferred embodiment of the invention. Generally, peptides and variants (at least those containing peptide linkages between amino acid residues) may be synthesised by the Fmoc-polyamide mode of solid-phase peptide synthesis as disclosed by Lu et al. (1981) and references therein. Temporary N-amino group protection is afforded by the 9-fluorenylmethyloxycarbonyl (Fmoc) group. Repetitive cleavage of this highly base-labile protecting group is done using 20% piperidine in N, N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalising agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N, N-dicyclohexyl-carbodiimide/1hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used are ethandithiol, phenol, anisole and water, the exact choice depending on the constituent amino acids of the peptide being synthesized. Also a combination of solid phase and solution phase methodologies for the synthesis of peptides is possible (see, for example, Bruckdorfer et al. 2004 and the references as cited therein).

Trifluoroacetic acid is removed by evaporation in vacuo, with subsequent trituration with diethyl ether affording the crude peptide. Any scavengers present are removed by a simple extraction procedure that upon lyophilisation of the aqueous phase affords the crude peptide free of scavengers. Reagents for peptide synthesis are generally available from e.g. Calbiochem-Novabiochem (UK) Ltd, Nottingham NG7 2QJ, UK.

Purification may be performed by any one, or a combination of, techniques such as re-crystallization, size exclusion chromatography, ion-exchange chromatography, hydrophobic interaction chromatography and (usually) reverse-phase high performance liquid chromatography using e.g. acetonitril/water gradient separation.

Analysis of peptides may be carried out using thin layer chromatography, electrophoresis, in particular capillary electrophoresis, solid phase extraction (CSPE), reverse-phase high performance liquid chromatography, amino-acid analysis after acid hydrolysis and by fast atom bombardment (FAB) mass spectrometric analysis, as well as MALDI and ESI-Q-TOF mass spectrometric analysis.

A further aspect of the invention provides a nucleic acid (e.g. polynucleotide) encoding a peptide or variant of the invention. The polynucleotide may be e.g. DNA, cDNA, PNA, CNA, RNA or combinations thereof, either single- and/or double-stranded, or native or stabilized forms of polynucleotides, such as e.g. polynucleotides with a phosphorothioate backbone, and it may or may not contain introns so long as it codes for the peptide. Of course, only peptides containing naturally occurring amino acid residues joined by naturally occurring peptide bonds are encodable by a polynucleotide. A still further aspect of the invention provides an expression vector capable of expressing a polypeptide according to the invention.

A variety of methods have been developed to link polynucleotides, especially DNA, to vectors for example via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. Synthetic linkers containing a variety of restriction endonuclease sites are commercially available from a number of sources including International Biotechnologies Inc, New Haven, Conn., USA.

A desirable method of modifying the DNA encoding the polypeptide of the invention utilizes the polymerase chain reaction as disclosed by (Saiki et al. (1988)). This method may be used for introducing the DNA into a suitable vector, for example by engineering in suitable restriction sites, or it may be used to modify the DNA in other useful ways as is known in the art.

If viral vectors are used, pox- or adenovirus vectors are preferred. The DNA (or in the case of retroviral vectors, RNA) may then be expressed in a suitable host to produce a polypeptide comprising the peptide or variant of the invention. Thus, the DNA encoding the peptide or variant of the invention may be used in accordance with known techniques, appropriately modified in view of the teachings contained herein, to construct an expression vector, which is then used to transform an appropriate host cell for the expression and production of the polypeptide of the invention. Such techniques include those disclosed in U.S. Pat. No. 4,440,859 issued 3 Apr. 1984 to Rutter et al., U.S. Pat. No. 4,530,901 issued 23 Jul. 1985 to Weissman, U.S. Pat. No. 4,582,800 issued 15 Apr. 1986 to Crowl, U.S. Pat. No. 4,677,063 issued 30 Jun. 1987 to Mark et al., U.S. Pat. No. 4,678,751 issued 7 Jul. 1987 to Goeddel, U.S. Pat. No. 4,704,362 issued 3 Nov. 1987 to Itakura et al., U.S. Pat. No.

4,710,463 issued 1 Dec. 1987 to Murray, U.S. Pat. No. 4,757,006 issued 12 Jul. 1988 to Toole, Jr. et al., U.S. Pat. No. 4,766,075 issued 23 Aug. 1988 to Goeddel et al. and U.S. Pat. No. 4,810,648 issued 7 Mar. 1989 to Stalker, all of which are incorporated herein by reference.

The DNA (or in the case of retroviral vectors, RNA) encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance.

Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example *Aspergillus* spec.), plant cells, animal cells and insect cells. Preferably, the system can be mammalian cells such as CHO cells available from the ATCC Cell Biology Collection.

A typical mammalian cell vector plasmid for constitutive expression comprises the CMV or SV40 promoter with a suitable poly A tail and a resistance marker, such as neomycin. One example is pSVL available from Pharmacia, Piscataway, N.J., USA. An example of an inducible mammalian expression vector is pMSG, also available from Pharmacia. Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (Ycps). CMV promoter-based vectors (for example from from Sigma-Aldrich) provide transient or stable expression, cytoplasmic expression or secretion, and N-terminal or C-terminal tagging in various combinations of FLAG, 3×FLAG, c-myc or MAT. These fusion proteins allow for detection, purification and analysis of recombinant protein. Dual-tagged fusions provide flexibility in detection.

The strong human cytomegalovirus (CMV) promoter regulatory region drives constitutive protein expression levels as high as 1 mg/L in COS cells. For less potent cell lines, protein levels are typically ~0.1 mg/L. The presence of the SV40 replication origin will result in high levels of DNA replication in SV40 replication permissive COS cells. CMV vectors, for example, can contain the pMB1 (derivative of pBR322) origin for replication in bacterial cells, the b-lactamase gene for ampicillin resistance selection in bacteria, hGH polyA, and the fl origin. Vectors containing the pre-protrypsin leader (PPT) sequence can direct the secretion of FLAG fusion proteins into the culture medium for purification using ANTI-FLAG antibodies, resins, and plates. Other vectors and expression systems are well known in the art for use with a variety of host cells.

The present invention also relates to a host cell transformed with a polynucleotide vector construct of the present invention. The host cell can be either prokaryotic or eukaryotic. Bacterial cells may be preferred prokaryotic host cells in some circumstances and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells, preferably vertebrate cells such as those from a mouse, rat, monkey or human fibroblastic and colon cell lines. Yeast host cells include YPH499, YPH500 and YPH501 which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells which are human embryonic kidney cells. Preferred insect cells are Sf9 cells which can be transfected with baculovirus expression vectors. An overview regarding the choice of suitable host cells for expression can be found in, for example, the textbook of Paulina Balbás and Argelia Lorence "Methods in Molecular Biology Recombinant Gene Expression, Reviews and Protocols," Part One, Second Edition, ISBN 978-1-58829-262-9, and other literature known to the person of skill.

Transformation of appropriate cell hosts with a DNA construct of the present invention is accomplished by well known methods that typically depend on the type of vector used. With regard to transformation of prokaryotic host cells, see, for example, Cohen et al. (1972) Proc. Natl. Acad. Sci. USA 69, 2110 and Sambrook et al. (1989) Molecular Cloning, A Laboratory Manual, Cold Spring Harbor Laboratory, Cold Spring Harbor, N.Y. Transformation of yeast cells is described in Sherman et al. (1986) Methods In Yeast Genetics, A Laboratory Manual, Cold Spring Harbor, N.Y. The method of Beggs (1978) Nature 275, 104-109 is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA. Electroporation is also useful for transforming and/or transfecting cells and is well known in the art for transforming yeast cell, bacterial cells, insect cells and vertebrate cells.

Successfully transformed cells, i.e. cells that contain a DNA construct of the present invention, can be identified by well known techniques such as PCR. Alternatively, the presence of the protein in the supernatant can be detected using antibodies.

It will be appreciated that certain host cells of the invention are useful in the preparation of the peptides of the invention, for example bacterial, yeast and insect cells. However, other host cells may be useful in certain therapeutic methods. For example, antigen-presenting cells, such as dendritic cells, may be used to express the peptides of the invention such that they may be loaded into appropriate MHC molecules. Thus, the present invention provides a host cell comprising a nucleic acid or an expression vector according to the invention.

In a preferred embodiment the host cell is an antigen presenting cell, in particular a dendritic cell or antigen presenting cell. APCs loaded with a recombinant fusion protein containing prostatic acid phosphatase (PAP) are currently under investigation for the treatment of prostate cancer (Sipuleucel-T) (Small E J et al. 2006; Rini et al. 2006).

A further aspect of the invention provides a method of producing a peptide or its variant. The method comprises culturing a host cell and isolating the peptide from the host cell or its culture medium.

In another embodiment the peptide, the nucleic acid or the expression vector of the invention are used in medicine. For example, the peptide or its variant may be prepared for intravenous (i.v.) injection, sub-cutaneous (s.c.) injection, intradermal (i.d.) injection, intraperitoneal (i.p.) injection, intramuscular (i.m.) injection. Preferred methods of peptide injection include s.c., i.d., i.p., i.m., and i.v. Preferred methods of DNA injection include i.d., i.m., s.c., i.p. and i.v. Doses of between 50 μg and 1.5 mg, preferably 125 μg to 500 μg, of peptide or DNA may be given and will depend on the respective peptide or DNA. Doses of this range were successfully used in previous trials (Brunsvig et al. 2006; Staehler et al. 2007).

Another aspect of the present invention includes an in vitro method for producing activated T cells, the method comprising contacting in vitro T cells with antigen loaded human class I or II MHC molecules expressed on the surface of a suitable antigen-presenting cell for a period of time sufficient to activate the T cell in an antigen specific manner. The antigen is a peptide according to the invention. Preferably a sufficient amount of the antigen is used with an antigen-presenting cell.

In the case of a MHC class II epitope used as an antigen, the T cells are CD4-positive helper cells, preferably of $T_{H1}$-type. The MHC class II molecules may be expressed on the surface of any suitable cell. Preferably the cell does not naturally express MHC class II molecules (in which case the cell has been transfected to express such a molecule. Alternatively, if the cell naturally expresses MHC class II molecules, it is preferred that it is defective in the antigen-processing or antigen-presenting pathways. In this way, it is possible for the cell expressing the MHC class II molecule to be completely loaded with a chosen peptide antigen before activating the T cell.

The antigen-presenting cell (or stimulator cell) typically has MHC class II molecules on its surface and preferably is itself substantially incapable of loading the MHC class II molecule with the selected antigen. The MHC class II molecule may readily be loaded with the selected antigen in vitro.

Preferably the mammalian cell lacks or has a reduced level or function of the TAP peptide transporter. Suitable cells that lack the TAP peptide transporter include T2, RMA-S and *Drosophila* cells. TAP is the Transporter associated with Antigen Processing.

The human peptide loading deficient cell line T2 is available from the American Type Culture Collection, 12301 Parklawn Drive, Rockville, Md. 20852, USA under Catalogue No CRL 1992; the *Drosophila* cell line Schneider line 2 is available from the ATCC under Catalogue No CRL 19863; the mouse RMA-S cell line is described in Karre et al. 1985.

The host cell preferably expresses substantially no MHC class I molecules before transfection. If the stimulator cell expresses a MHC molecule it is preferred that that the molecule is important for providing a co-stimulatory signal for T-cells such as any of B7.1, B7.2, ICAM-1 and LFA 3.

The nucleic acid sequences of numerous MHC class II molecules, and of the costimulator molecules, are publicly available from the GenBank and EMBL databases.

Similarly, in when a MHC class I epitope is used as an antigen, the T cells are CD8-positive CTLs.

If an antigen-presenting cell is transfected to express such an epitope, preferably the cell comprises an expression vector capable of expressing a peptide containing SEQ ID NO: 1 to SEQ ID NO: 11 or its variant amino acid sequence.

A number of other methods may be used for generating CTL in vitro. For example, the methods described in Peoples et al. (1995) and Kawakami et al. (1992) use autologous tumor-infiltrating lymphocytes in the generation of CTL. Plebanski et al. (1995) makes use of autologous peripheral blood lymphocytes (PLBs) in the preparation of CTL. Jochmus et al. (1997) describes the production of autologous CTL by pulsing dendritic cells with peptide or polypeptide, or via infection with recombinant virus. Hill et al. (1995) and Jerome et al. (1993) employ B cells in the production of autologous CTL. In addition, macrophages pulsed with peptide or polypeptide, or infected with recombinant virus, may be used in the preparation of autologous CTL. S. Walter et al. (2003) describe the in vitro priming of T cells by using artificial antigen presenting cells (aAPCs), which is also a suitable method for generating T cells against the peptide of choice. In this study, aAPCs were generated by the coupling of preformed MHC:peptide complexes to the surface of polystyrene particles (microbeads) by biotin:streptavidin biochemistry. This system permits the exact control of the MHC density on aAPCs, which allows one to selectively elicit high- or low-avidity antigen-specific T cell responses with high efficiency from blood samples. Apart from MHC:peptide complexes, aAPCs should carry other proteins with co-stimulatory activity like anti-CD28 antibodies coupled to their surface. Furthermore such aAPC-based system often requires the addition of appropriate soluble factors, e. g. cytokines like interleukin-12.

Allogeneic cells may also be used in the preparation of T cells and a method is described in detail in WO 97/26328, incorporated herein by reference. For example, in addition to *Drosophila* cells and T2 cells, other cells may be used to present antigens such as CHO cells, baculovirus-infected insect cells, bacteria, yeast, vaccinia-infected target cells. In addition plant viruses may be used. See for example, Porta et al (1994), which describes the development of cowpea mosaic virus as a high-yielding system for the presentation of foreign peptides.

The activated T cells that are directed against the peptides of the invention are useful in therapy. Thus, a further aspect of the invention provides activated T cells obtainable by the foregoing methods of the invention.

Activated T cells that are produced by the above method will selectively recognize a cell that aberrantly expresses a polypeptide that comprises an amino acid sequence of SEQ ID NO: 1 to 11.

Preferably, the T cell recognizes the cell by interacting through its TCR with the HLA/peptide-complex (for example, binding). The T cells are useful in a method of killing target cells in a patient whose target cells aberrantly express a polypeptide comprising an amino acid sequence of the invention wherein the patient is administered an effective number of the activated T cells. The T cells that are administered to the patient may be derived from the patient and activated as described above (i.e. they are autologous T cells). Alternatively, the T cells are not from the patient but are from another individual. Of course, it is preferred if the individual is a healthy individual. By "healthy individual" the inventors mean that the individual is generally in good health, preferably has a competent immune system and, more preferably, is not suffering from any disease which can be readily tested for and detected.

In vivo, the target cells for the CD4-positive T cells according to the present invention can be cells of the tumor (which sometimes express MHC class II) and/or stromal cells surrounding the tumor (tumor cells) (which sometimes also express MHC class II; (Dengjel et al., 2006)).

The T cells of the invention may be used as active ingredients of a therapeutic composition. Thus, the invention also provides a method of killing target cells in a patient whose target cells aberrantly express a polypeptide comprising an amino acid sequence of the invention. The method comprises administering to the patient an effective number of T cells as defined above.

By "aberrantly expressed" it is meant that the polypeptide is over-expressed compared to normal levels of expression or that the gene is silent in the tissue from which the tumor is derived but in the tumor it is expressed. By "over-expressed" it is meant that the polypeptide is present at a level at least 1.2× that present in normal tissue; preferably at least 2× and more preferably at least 5× or 10× the level present in normal tissue.

T cells may be obtained by methods known in the art, e.g. those described above.

Protocols for this so-called adoptive transfer of T cells are well known in the art and can be found, e.g. in (Rosenberg et al., 1987; Rosenberg et al., 1988; Dudley et al., 2002; Yee et al., 2002; Dudley et al., 2005); reviewed in (Gattinoni et al., 2006) and (Morgan et al., 2006).

Any molecule of the invention, i.e. the peptide, nucleic acid, expression vector, cell, activated CTL, T-cell receptor or the nucleic acid encoding it is useful for the treatment of disorders characterised by cells escaping an immune response. Therefore any molecule of the present invention may be used as medicament or in the manufacture of a medicament. The molecule may be used by itself or combined with other molecule(s) of the invention or (a) known molecule(s).

Preferably the medicament of the present invention is a vaccine. It may be administered directly into the patient, into the affected organ or systemically i.d., i.m., s.c., i.p. and i.v., or applied ex vivo to cells derived from the patient or a human cell line, which are subsequently administered to the patient, or used in vitro to select a subpopulation of immune cells derived from the patient, which are then re-administered to the patient. If the nucleic acid is administered to cells in vitro, it may be useful for the cells to be transfected so as to co-express immune-stimulating cytokines, such as interleukin-2. The peptide may be substantially pure, or combined with an immune-stimulating adjuvant (see below) or used in combination with immune-stimulatory cytokines, or be administered with a suitable delivery system, for example liposomes. The peptide may also be conjugated to a suitable carrier such as keyhole limpet haemocyanin (KLH) or mannan (see WO 95/18145 and Longenecker et al. (1993)). The peptide may also be tagged, may be a fusion protein, or may be a hybrid molecule. The peptides whose sequence is given in the present invention are expected to stimulate CD4 or CD8 T cells. However, stimulation of CD8 CTLs is more efficient in the presence of CD4 T-helper cells. Thus, for MHC Class I epitopes that stimulate CD8 CTL the fusion partner or sections of a hybrid molecule suitably provide epitopes that stimulate CD4-positive T cells. CD4- and CD8-stimulating epitopes are well known in the art and include those identified in the present invention.

In one aspect the vaccine comprises at least one peptide, preferably two to 50, more preferably two to 25, even more preferably two to 15 and most preferably two, three, four, five, six, seven, eight, nine, ten, eleven, twelve or thirteen peptides. The peptide(s) may be derived from one or more specific TAAs and may bind to MHC class I and/or class II molecules.

Preferably when the peptides of the invention are used in a vaccine or medicament of the invention, they are present as a salt, such as for example, but not limited to an acetate salt or a chloride salt.

The polynucleotide may be substantially pure, or contained in a suitable vector or delivery system. The nucleic acid may be DNA, cDNA, PNA, CNA, RNA or a combination thereof. Methods for designing and introducing such a nucleic acid are well known in the art. An overview is provided by e.g. Pascolo S. 2006; Stan R. 2006, or A Mahdavi 2006. Polynucleotide vaccines are easy to prepare, but the mode of action of these vectors in inducing an immune response is not fully understood. Suitable vectors and delivery systems include viral DNA and/or RNA, such as systems based on adenovirus, vaccinia virus, retroviruses, herpes virus, adeno-associated virus or hybrids containing elements of more than one virus. Non-viral delivery systems include cationic lipids and cationic polymers and are well known in the art of DNA delivery. Physical delivery, such as via a "gene-gun," may also be used. The peptide or peptides encoded by the nucleic acid may be a fusion protein, for example with an epitope that stimulates T cells for the respective opposite CDR as noted above.

The medicament of the invention may also include one or more adjuvants. Adjuvants are substances that non-specifically enhance or potentiate the immune response (e.g., immune responses mediated by CTLs and helper-T ($T_H$) cells to an antigen, and would thus be considered useful in the medicament of the present invention. Suitable adjuvants include, but are not limited to 1018 ISS, aluminium salts, Amplivax, AS15, BCG, CP-870,893, CpG7909, CyaA, dSLIM, flagellin or TLR5 ligands derived from flagellin, FLT3 ligand, GM-CSF, IC30, IC31, Imiquimod (ALDARA), ImuFact IMP321, Interferon-alpha or -beta, or pegylated derivatives thereof, IS Patch, ISS, ISCOMATRIX, ISCOMs, JuvImmune, LipoVac, MALP2, MF59, monophosphoryl lipid A, Montanide IMS 1312, Montanide ISA 206, Montanide ISA 50V, Montanide ISA-51, water-in-oil and oil-in-water emulsions, OK-432, OM-174, OM-197-MP-EC, ONTAK, OspA, PepTel vector system, PLG microparticles, resiquimod, SRL172, Virosomes and other Virus-like particles, YF-17D, VEGF trap, R848, beta-glucan, Pam3Cys, Aquila's QS21 stimulon, which is derived from saponin, mycobacterial extracts and synthetic bacterial cell wall mimics, and other proprietary adjuvants such as Ribi's Detox, Quil, or Superfos. Adjuvants such as Freund's or GM-CSF are preferred. Several immunological adjuvants (e.g., MF59) specific for dendritic cells and their preparation have been described previously (Dupuis M et al. 1998; Allison 1998). Also cytokines may be used. Several cytokines have been directly linked to influencing dendritic cell migration to lymphoid tissues (e.g., TNF-α), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12, IL-15, IL-23, IL-7, IFN-alpha, IFN-beta) (Gabrilovich et al. 1996).

CpG immunostimulatory oligonucleotides have also been reported to enhance the effects of adjuvants in a vaccine setting. Without bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly it enhances dendritic cell maturation and differentiation, resulting in enhanced activation of $T_{H1}$ cells and strong cytotoxic T-lymphocyte (CTL) generation, even in the absence of CD4 T cell help. The $T_{H1}$ bias induced by TLR9 stimulation is maintained even in the presence of vaccine adjuvants such as alum or incomplete Freund's adjuvant (IFA) that normally promote a $T_{H2}$ bias. CpG oligonucleotides show even greater adjuvant activity when formulated or co-administered with other adjuvants or in formulations such as microparticles, nano particles, lipid emulsions or similar formulations, which are especially necessary for inducing a strong response when the antigen is relatively weak. They also accelerate the immune response and enable the antigen doses to be reduced by approximately two orders of magnitude, with comparable antibody responses to the full-dose vaccine without CpG in some experiments (Krieg et al. 2006). U.S. Pat. No. 6,406,705 B1 describes the combined use of CpG oligonucleotides, non-nucleic acid adjuvants and an antigen to induce an antigen-specific immune response. A CpG TLR9 antagonist is dSLIM (double Stem Loop Immunomodulator) by Mologen (Berlin, Germany) which is a preferred component of the pharmaceutical composition of the present invention. Other TLR binding molecules such as RNA binding TLR 7, TLR 8 and/or TLR 9 may also be used.

Other examples for useful adjuvants include, but are not limited to chemically modified CpGs (e.g. CpR, Idera), dsRNA analogues such as Poly(I:C) and AmpliGen, non-CpG bacterial DNA or RNA as well as immunoactive small molecules and antibodies such as cyclophosphamide, sunitinib, bevacizumab, celebrex, NCX-4016, sildenafil, tadalafil, vardenafil, sorafenib, temozolomide, temsirolimus, XL-999, CP-547632, pazopanib, VEGF Trap, ZD2171, AZD2171, anti-CTLA4 and SC58175, which may act therapeutically and/or as an adjuvant. The amounts and concentrations of adjuvants and additives useful in the context of the present invention can readily be determined by the skilled artisan without undue experimentation.

Preferred adjuvants are dSLIM, Interferon-alpha, -beta, CpG7909, IC31, ALDARA (Imiquimod), PeviTer, RNA, tadalafil, temozolomide, and JuvImmune.

The present invention provides a medicament that useful in treating cancer, preferably neuronal cancer, and most preferably brain cancer. The cancer may be non-metastatic or metastatic, in particular it may be astrocytoma, pilocytic astrocytoma, dysembryoplastic neuroepithelial tumor, oligodendrogliomas, ependymoma, glioblastoma multiforme, mixed gliomas, oligoastrocytomas, medulloblastoma, retinoblastoma, neuroblastoma, germinoma, teratoma, gangliogliomas, gangliocytoma, central gangliocytoma, primitive neuroectodermal tumors (PNET, e.g. medulloblastoma, medulloepithelioma, neuroblastoma, retinoblastoma, ependymoblastoma), tumors of the pineal parenchyma (e.g. pineocytoma, pineoblastoma), ependymal cell tumors, choroid plexus tumors, neuroepithelial tumors of uncertain origin (e.g. gliomatosis cerebri, astroblastoma) or glioblastoma.

Since the peptides of the invention were isolated from glioblastoma, and in the case of SEQ ID NO:2 also from adenosquamous carcinoma, the medicament of the invention is preferably used to treat glioblastoma or adenosquamous carcinoma.

In addition to being useful for treating cancer, the peptides of the present invention are also useful as diagnostics. Since the peptides were generated from glioblastoma or in the case of SEQ ID NO:2 also isolated from adenousquamous carcinoma, and since it was determined that these peptides are not present in normal tissues, these peptides can be used to diagnose the presence of these types of cancer.

The presence of the peptides of the present invention on tissue biopsies can assist a pathologist in diagnosis of cancer. Detection of certain peptides of the present invention by means of antibodies, mass spectrometry or other methods known in the art can inform the pathologist whether the tissue is malignant, inflamed or generally diseased. The presence of groups of peptides of the present invention can enable classification or subclassification of diseased tissues.

The detection of the peptides of the present invention on diseased tissue specimen can enable the decision about the benefit of therapies involving the immune system, especially if T lymphocytes are known or expected to be involved in the mechanism of action. Loss of MHC expression is a well described mechanism by which infected of malignant cells escape immunosurveillance. Thus, presence of the peptides of the present invention shows that this mechanism is not exploited by the analyzed cells.

The peptides of the present invention may be used to analyze lymphocyte responses against those peptides of the present invention, such as T cell responses or antibody responses against the peptides of the present invention or the peptides of the present invention complexed to MHC molecules. These lymphocyte responses can be used as prognostic markers for decision on further therapy steps. These responses can also be used as surrogate markers in immunotherapy approaches aiming to induce lymphocyte responses by different means, e.g. vaccination of protein, nucleic acids, autologous materials, adoptive transfer of lymphocytes. In gene therapy settings, lymphocyte responses against the peptides of the present invention can be considered in the assessment of side effects. Monitoring of lymphocyte responses might also be a valuable tool for follow-up examinations of transplantation therapies, e.g. for the detection of graft versus host and host versus graft diseases.

The peptides of the present invention can be used to generate and develop specific antibodies against MHC/peptide complexes. These can be used for therapy, targeting toxins or radioactive substances to the diseased tissue. Another use of these antibodies can be targeting radionuclides to the diseased tissue for imaging purposes, such as PET. This use can help to detect small metastases or to determine the size and precise localization of diseased tissues. In addition, the peptides can be used to verify a pathologist's diagnosis of a cancer based on a biopsied sample.

In yet another aspect thereof, the present invention relates to a kit comprising (a) a container that contains a pharmaceutical composition as described above, in solution or in lyophilized form; (b) optionally, a second container containing a diluent or reconstituting solution for the lyophilized formulation; and (c) optionally, instructions for (i) use of the solution or (ii) reconstitution and/or use of the lyophilized formulation. The kit may further comprise one or more of (iii) a buffer, (iv) a diluent, (v) a filter, (vi) a needle, or (v) a syringe. The container is preferably a bottle, a vial, a syringe or test tube; and it may be a multi-use container. The pharmaceutical composition is preferably lyophilized.

Kits of the present invention preferably comprise a lyophilized formulation of the present invention in a suitable container and instructions for its reconstitution and/or use. Suitable containers include, for example, bottles, vials (e.g. dual chamber vials), syringes (such as dual chamber syringes) and test tubes. The container may be formed from a variety of materials such as glass or plastic. Preferably the kit and/or container contains instructions on or associated with the container that indicates directions for reconstitution and/or use. For example, the label may indicate that the lyophilized formulation is to reconstituted to peptide concentrations as described above. The label may further indicate that the formulation is useful or intended for subcutaneous administration.

The container holding the formulation may be a multi-use vial, which allows for repeat administrations (e.g., from 2-6 administrations) of the reconstituted formulation. The kit may further comprise a second container comprising a suitable diluent (e.g., sodium bicarbonate solution).

Upon mixing of the diluent and the lyophilized formulation, the final peptide concentration in the reconstituted formulation is preferably at least 0.15 mg/mL/peptide (=75 µg) and preferably not more than 3 mg/mL/peptide (=1500 µg). The kit may further include other materials desirable from a commercial and user standpoint, including other buffers, diluents, filters, needles, syringes, and package inserts with instructions for use.

Kits of the present invention may have a single container that contains the formulation of the pharmaceutical compositions according to the present invention with or without other components (e.g., other compounds or pharmaceutical compositions of these other compounds) or may have a distinct container for each component.

Preferably, kits of the invention include a formulation of the invention packaged for use in combination with the co-administration of a second compound (such as adjuvants (e.g. GM-CSF), a chemotherapeutic agent, a natural product, a hormone or antagonist, a anti-angiogenesis agent or inhibitor, a apoptosis-inducing agent or a chelator) or a pharmaceutical composition thereof. The components of the kit may be pre-complexed or each component may be in a separate distinct container prior to administration to a patient. The components of the kit may be provided in one or more liquid solutions, preferably, an aqueous solution, more preferably, a sterile aqueous solution. The components of the kit may also be provided as solids, which may be converted into liquids by addition of suitable solvents, which are preferably provided in another distinct container.

The container of a therapeutic kit may be a vial, test tube, flask, bottle, syringe, or any other means of enclosing a solid or liquid. Usually, when there is more than one component, the kit will contain a second vial or other container, which allows for separate dosing. The kit may also contain another container for a pharmaceutically acceptable liquid. Preferably, a therapeutic kit will contain an apparatus (e.g., one or more needles, syringes, eye droppers, pipette, etc.), which enables administration of the agents of the invention that are components of the present kit.

The pharmaceutical formulation of the present invention is one that is suitable for administration of the peptides by any acceptable route such as oral (enteral), nasal, ophthal, subcutaneous, intradermal, intramuscular, intravenous or transdermal. Preferably the administration is s.c., and most preferably, i.d. Administration may be by infusion pump.

Definitions

As used herein and except as noted otherwise, all terms are defined as given below.

The term "peptide" is used herein to designate a series of amino acid residues, connected one to the other typically by peptide bonds between the alpha-amino and carbonyl groups of the adjacent amino acids. The peptides are typically 9 amino acids in length, but can be as short as 8 amino acids in length, and as long as 14 amino acids in length.

The term "oligopeptide" is used herein to designate a series of amino acid residues, connected one to the other typically by peptide bonds between the alpha-amino and carbonyl groups of the adjacent amino acids. The length of the oligopeptide is not critical to the invention as long as the correct epitope or epitopes are maintained therein. The oligopeptides are typically less than about 30 amino acid residues in length, and greater than about 14 amino acids in length.

The term "polypeptide" designates a series of amino acid residues, connected one to the other typically by peptide bonds between the alpha-amino and carbonyl groups of the adjacent amino acids. The length of the polypeptide is not critical to the invention as long as the correct epitopes are maintained. In contrast to the terms peptide or oligopeptide, the term polypeptide is meant to refer to protein molecules of longer than about 30 residues in length.

A peptide, oligopeptide, protein, or polynucleotide coding for such a molecule is "immunogenic" (and thus an "immunogen" within the present invention), if it is capable of inducing an immune response. In the case of the present invention, immunogenicity is more specifically defined as the ability to induce a CTL-mediated response. Thus, an "immunogen" would be a molecule that is capable of inducing an immune response, and in the case of the present invention, a molecule capable of inducing a CTL response.

A T cell "epitope" is a short peptide molecule that binds to a class I or II MHC molecule and that is subsequently recognized by a T cell. T cell epitopes that bind to class I MHC molecules are typically 8-14 amino acids in length, and most typically 9 amino acids in length. T cell epitopes that bind to class II MHC molecules are typically 12-30 amino acids in length. In the case of epitopes that bind to class II MHC molecules, the same T cell epitope may share a common core segment, but differ in the length of the carboxy- and amino-terminal flanking sequences due to the fact that ends of the peptide molecule are not buried in the structure of the class II MHC molecule peptide-binding cleft as they are in the class I MHC molecule peptide-binding cleft.

There are three different genetic loci that encode for MHC class 1 molecules: HLA-A, HLA-B, and HLA-C. HLA-A1, HLA-A2, and HLA-A11 are examples of different class I MHC molecules that can be expressed from these loci.

As used herein, reference to a DNA sequence includes both single stranded and double stranded DNA. Thus, the specific sequence, unless the context indicates otherwise, refers to the single strand DNA of such sequence, the duplex of such sequence with its complement (double stranded DNA) and the complement of such sequence.

The term "coding region" refers to that portion of a gene which either naturally or normally codes for the expression product of that gene in its natural genomic environment, i.e., the region coding in vivo for the native expression product of the gene.

The coding region can be from a normal, mutated or altered gene, or can even be from a DNA sequence, or gene, wholly synthesized in the laboratory using methods well known to those of skill in the art of DNA synthesis.

The term "nucleotide sequence" refers to a heteropolymer of deoxyribonucleotides.

The nucleotide sequence encoding for a particular peptide, oligopeptide, or polypeptide may be naturally occurring or they may be synthetically constructed. Generally, DNA segments encoding the peptides, polypeptides, and proteins of this invention are assembled from cDNA fragments and short oligonucleotide linkers, or from a series of oligonucleotides, to provide a synthetic gene which is capable of being expressed in a recombinant transcriptional unit comprising regulatory elements derived from a microbial or viral operon.

The term "expression product" means the polypeptide or protein that is the natural translation product of the gene and any nucleic acid sequence coding equivalents resulting from genetic code degeneracy and thus coding for the same amino acid(s).

The term "fragment," when referring to a coding sequence, means a portion of nucleic acid comprising less than the complete coding region whose expression product retains essentially the same biological function or activity as the expression product of the complete coding region.

The term "DNA segment" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the segment and its component nucleotide sequences by standard biochemical methods, for example, by using a cloning vector. Such segments are provided in the form of an open reading frame uninterrupted by internal nontranslated sequences, or introns, which are typically present in eukaryotic genes. Sequences of non-translated DNA may be present downstream from the open reading frame, where the same do not interfere with manipulation or expression of the coding regions.

The term "primer" means a short nucleic acid sequence that is paired with one strand of DNA and provides a free 3'OH end at which a DNA polymerase starts synthesis of a deoxyribonucleotide chain.

The term "promoter" means a region of DNA involved in binding of RNA polymerase to initiate transcription.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polynucleotides, and recombinant or immunogenic polypeptides, disclosed in accordance with the present invention may also be in "purified" form. The term "purified" does not require absolute purity; rather, it is intended as a relative definition, and can include preparations that are highly purified or preparations that are only partially purified, as those terms are understood by those of skill in the relevant art. For example, individual clones isolated from a cDNA library have been conventionally purified to electrophoretic homogeneity. Purification of starting material or natural material to at least one order of magnitude, preferably two or three orders, and more preferably four or five orders of magnitude is expressly contemplated. Furthermore, the claimed polypeptide which has a purity of preferably 99.999%, or at least 99.99% or 99.9%; and even desirably 99% by weight or greater is expressly contemplated.

The nucleic acids and polypeptide expression products disclosed according to the present invention, as well as expression vectors containing such nucleic acids and/or such polypeptides, may be in "enriched form." As used herein, the term "enriched" means that the concentration of the material is at least about 2, 5, 10, 100, or 1000 times its natural concentration (for example), advantageously 0.01%, by weight, preferably at least about 0.1% by weight. Enriched preparations of about 0.5%, 1%, 5%, 10%, and 20% by weight are also contemplated. The sequences, constructs, vectors, clones, and other materials comprising the present invention can advantageously be in enriched or isolated form.

The term "active fragment" means a fragment that generates an immune response (i.e., has immunogenic activity) when administered, alone or optionally with a suitable adjuvant, to an animal, such as a mammal, for example, a rabbit or a mouse, and also including a human, such immune response taking the form of stimulating a CTL response within the recipient animal, such as a human. Alternatively, the "active fragment" may also be used to induce a CTL response in vitro.

As used herein, the terms "portion," "segment," and "fragment," when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. This means that any such fragment will necessarily contain as part of its amino acid sequence a segment, fragment or portion, that is substantially identical, if not exactly identical, to a sequence of SEQ ID NO: 1 to 11, which correspond to the naturally occurring, or "parent" proteins of the SEQ ID NO: 1 to 11. When used in relation to polynucleotides, such terms refer to the products produced by treatment of the polynucleotides with any of the common endonucleases.

In accordance with the present invention, the term "percent identity" or "percent identical," when referring to a sequence, means that a sequence is compared to a claimed or described sequence after alignment of the sequence to be compared (the "Compared Sequence") with the described or claimed sequence (the "Reference Sequence"). The Percent Identity is then determined according to the following formula:

Percent Identity=100 [1−(C/R)] wherein C is the number of differences between the Reference Sequence and the Compared Sequence over the length of alignment between the Reference Sequence and the Compared Sequence wherein (i) each base or amino acid in the Reference Sequence that does not have a corresponding aligned base or amino acid in the Compared Sequence and (ii) each gap in the Reference Sequence and (iii) each aligned base or amino acid in the Reference Sequence that is different from an aligned base or amino acid in the Compared Sequence, constitutes a difference; and R is the number of bases or amino acids in the Reference Sequence over the length of the alignment with the Compared Sequence with any gap created in the Reference Sequence also counted as a base or amino acid.

If an alignment exists between the Compared Sequence and the Reference Sequence for which the percent identity as calculated above is about equal to or greater than a specified minimum Percent Identity, then the Compared Sequence has the specified minimum percent identity to the Reference Sequence, even though alignments may exist in which the herein above calculated Percent Identity is less than the specified Percent Identity.

The original peptides disclosed herein can be modified by the substitution of one or more residues at different, possibly selective, sites within the peptide chain. Such substitutions may be of a conservative nature, for example, where one amino acid is replaced by an amino acid of similar structure and characteristics, such as where a hydrophobic amino acid is replaced by another hydrophobic amino acid. Even more conservative would be replacement of amino acids of the same or similar size and chemical nature, such as where leucine is replaced by isoleucine. In studies of sequence variations in families of naturally occurring homologous proteins, certain amino acid substitutions are more often tolerated than others, and these are often show correlation with similarities in size, charge, polarity, and hydrophobicity between the original amino acid and its replacement, and such is the basis for defining "conservative substitutions."

Conservative substitutions are herein defined as exchanges within one of the following five groups: Group 1—small aliphatic, nonpolar or slightly polar residues (Ala, Ser, Thr, Pro, Gly); Group 2—polar, negatively charged residues and their amides (Asp, Asn, Glu, Gln); Group 3—polar, positively charged residues (His, Arg, Lys); Group 4—large, aliphatic, nonpolar residues (Met, Leu, lie, Val, Cys); and Group 5—large, aromatic residues (Phe, Tyr, Trp).

Less conservative substitutions might involve the replacement of one amino acid by another that has similar characteristics but is somewhat different in size, such as replacement of an alanine by an isoleucine residue. Highly nonconservative replacements might involve substituting an acidic amino acid for one that is polar, or even for one that is basic in character.

Such radical substitutions cannot, however, be dismissed as potentially ineffective since chemical effects are not totally predictable and radical substitutions might well give rise to serendipitous effects not otherwise predictable from simple chemical principles.

Of course, such substitutions may involve structures other than the common L-amino acids. Thus, D-amino acids might be substituted for the L-amino acids commonly found in the antigenic peptides of the invention and yet still be encompassed by the disclosure herein. In addition, amino acids possessing non-standard R groups (i.e., R groups other than those found in the common 20 amino acids of natural proteins) may also be used for substitution purposes to produce immunogens and immunogenic polypeptides according to the present invention.

If substitutions at more than one position are found to result in a peptide with substantially equivalent or greater antigenic activity as defined below, then combinations of those substitutions will be tested to determine if the combined substitutions result in additive or synergistic effects on the antigenicity of the peptide. At most, no more than four positions within the peptide would simultaneously be substituted.

The term "T-cell response" means the specific proliferation and activation of effector functions induced by a peptide in vitro or in vivo. For MHC class I restricted CTLs, effector functions may be lysis of peptide-pulsed, peptide-precursor pulsed or naturally peptide-presenting target cells, secretion of cytokines, preferably Interferon-gamma, TNF-alpha, or IL-2 induced by peptide, secretion of effector molecules, preferably granzymes or perforins induced by peptide, or degranulation. For MHC class II-restricted T helper cells, effector functions may be peptide induced secretion of cytokines, preferably, IFN-gamma, TNF-alpha, IL-4, IL5, IL-10, or IL-2, or peptide-induced degranulation. Possible effector functions for CTLs and T helper cells are not limited to this list.

Based on cytotoxicity assays, an epitope is considered substantially identical to the reference peptide if it has at least 10% of the antigenic activity of the reference peptide as defined by the ability of the substituted peptide to reconstitute the epitope recognized by a CTL in comparison to the reference peptide. Thus, when comparing the lytic activity in the linear portion of the effector:target curves with equimolar concentrations of the reference and substituted peptides, the observed percent specific killing of the target cells incubated with the substituted peptide should be equal to that of the reference peptide at an effector:target ratio that is no greater than 10-fold above the reference peptide effector:target ratio at which the comparison is made.

Preferably, when the CTLs specific for a peptide of SEQ ID NO: 1 to 11 are tested against the substituted peptides, the peptide concentration at which the substituted peptides achieve half the maximal increase in lysis relative to background is no more than about 1 mM, preferably no more than about 1 µM, more preferably no more than about 1 nM, and still more preferably no more than about 100 pM, and most preferably no more than about 10 pM. It is also preferred that the substituted peptide be recognized by CTLs from more than one individual, at least two, and more preferably three individuals.

Thus, the epitopes of the present invention may be identical to naturally occurring tumor-associated or tumor-specific epitopes or may include epitopes that differ by no more than four residues from the reference peptide, as long as they have substantially identical antigenic activity.

It should be understood that the features of the invention as disclosed and described herein can be used not only in the respective combination as indicated but also in a singular fashion without departing from the intended scope of the present invention. For the purposes of the present invention, all references as cited herein are incorporated by reference in their entireties.

The following examples are provided for illustrative purposes only and are not intended to limit the invention.

EXAMPLES

Example 1: Identification of Tumor Associated Peptides (TUMAPs) Presented on Cell Surface Tissue Samples Patients' tumor and healthy tissues were provided by Hôpital Cantonal Universitaire de Geneve (Medical Oncology Laboratory of Tumor Immunology) and Neurochirurgische Universitats-Klinik Heidelberg (Molekularbiologisches Labor). Written informed consents of all patients had been given before surgery. Tissues were shock-frozen in liquid nitrogen immediately after surgery and stored until isolation of TUMAPs at −80° C.

Isolation of HLA Peptides from Tissue Samples

HLA peptide pools from shock-frozen tissue samples were obtained by immune precipitation from solid tissues according to a slightly modified protocol (Falk, K. et al. 1991; Seeger, F. H. et al., 1999) using the HLA-A*02-specific antibody BB7.2 or the HLA-A, -B, -C-specific antibody W6/32, CNBr-activated sepharose, acid treatment and ultrafiltration.

Detection of TUMAPs by ESI-Liquid Chromatography Mass Spectrometry (ESI-LCMS)

Method One:

The obtained HLA peptide pools were separated according to their hydrophobicity by reversed-phase chromatography (CapLC, Waters) and the eluting peptides were analyzed in a hybrid quadrupole orthogonal acceleration time of flight tandem mass spectrometer (Q-TOF Ultima, Waters) equipped with an ESI source. Peptide pools were loaded onto a C18 pre-column for concentration and desalting. After loading, the pre-column was placed in line for separation by a fused-silica micro-capillary column (75 μm i.d.×250 mm) packed with 5 μm C18 reversed-phase material (Dionex). Solvent A was 4 mM ammonium acetate/water. Solvent B was 2 mM ammonium acetate in 80% acetonitrile/water. Both solvents were adjusted to pH 3.0 with formic acid. A binary gradient of 15% to 60% B within 90 minutes was performed, applying a flow rate of 5 μl/min reduced to approximately 200 nl/min by a split-system. A gold coated glass capillary (PicoTip, New Objective) was used for introduction into the micro-ESI source. The integration time for the TOF analyzer was 1.9 s with an interscan delay of 0.1 s. Subsequently, the peptide sequences were revealed by collisionally induced decay (CID) mass spectrometry (ESI-LCMS/MS). The identified TUMAP sequence was assured by comparison of the generated natural TUMAP fragmentation pattern with the fragmentation pattern of a synthetic sequence-identical reference peptide.

Method Two:

The obtained HLA peptide pools were separated according to their hydrophobicity by reversed-phase chromatography (Acquity UPLC system, Waters) and the eluting peptides were analyzed in LTQ-Orbitrap hybrid mass spectrometer (ThermoElectron) equipped with an ESI source. Peptide pools were loaded directly onto the analytical fused-silica micro-capillary column (75 μm i.d.×250 mm) packed with 1.7 μm C18 reversed-phase material (Waters) applying a flow rate of 400 nL per minute. Subsequently, the peptides were separated using an two-step 180 minute-binary gradient from 10% to 33% B at flow rates of 300 nL per minute. The gradient was composed of Solvent A (0.1% formic acid in water) and solvent B (0.1% formic acid in acetonitrile). A gold coated glass capillary (PicoTip, New Objective) was used for introduction into the micro-ESI source. The LTQ-Orbitrap mass spectrometer was operated in the data-dependent mode using a TOP5 strategy. In brief, a scan cycle was initiated with a full scan of high mass accuracy in the orbitrap (R=30,000), which was followed by MS/MS scans also in the orbitrap (R=7500) on the 5 most abundant precursor ions with dynamic exclusion of previously selected ions. Tandem mass spectra were interpreted by SEQUEST and additional manual control. The identified TUMAP sequence was assured by comparison of the generated natural TUMAP fragmentation pattern with the fragmentation pattern of a synthetic sequence-identical reference peptide.

Figure 1B:
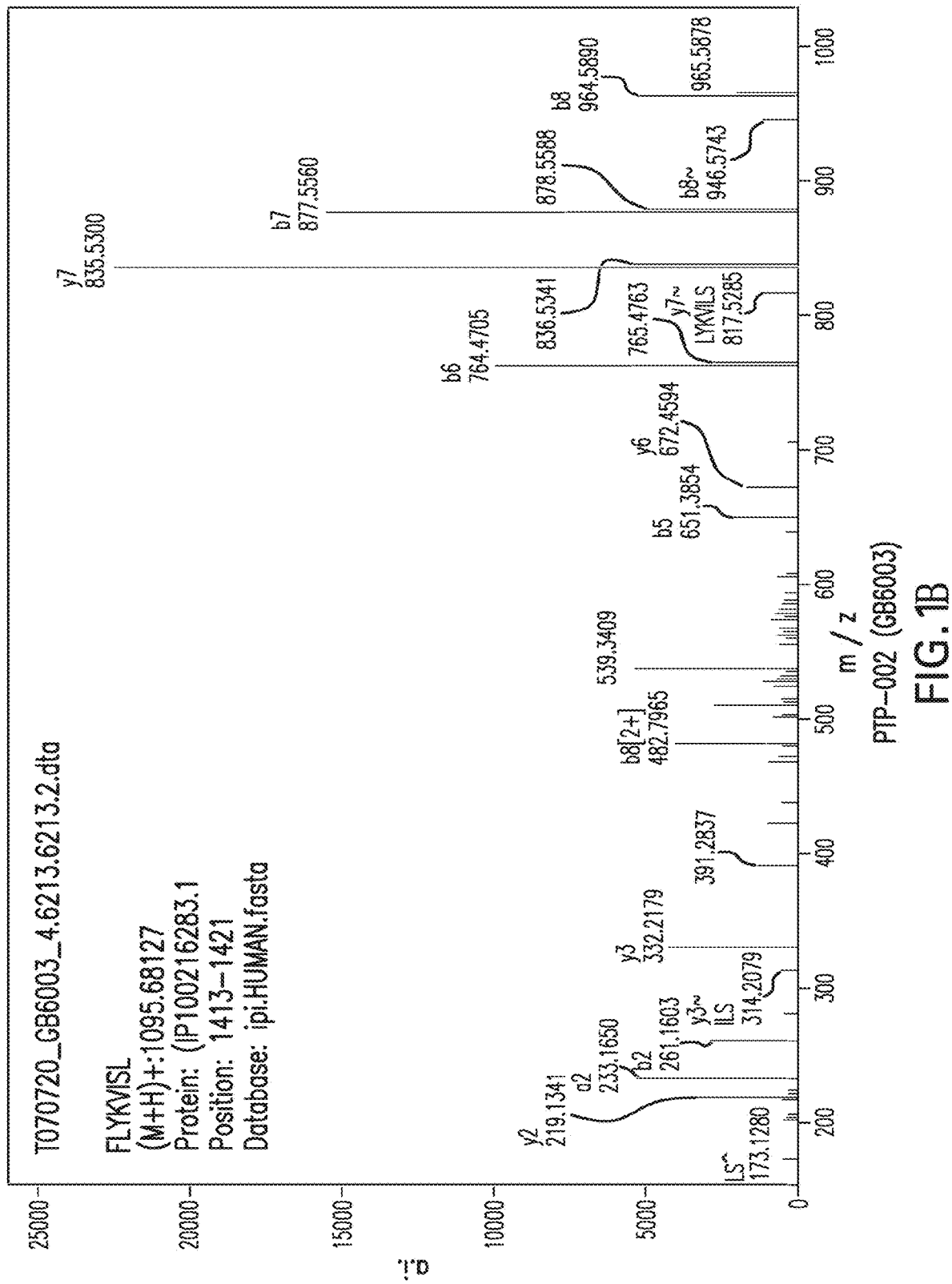

FIGS. 1a and 1b show exemplary spectra obtained from tumor tissue for MHC class I associated TUMAPs.

TABLE 3

List of tumor samples on which the peptides were identified

| SEQ ID NO | Peptide Code | Tumor Sources |
|---|---|---|
| 1 | PTP-001 | GB1006T, GB1012T |
| 2 | PTP-002 | GB1023T, GB6003T |
| 3 | PTP-003 | GB1008T, GB1011T, GB1012T, GB1014T, GB1020T, GB1021T, GB1023T, GB1026T, GB6003T, GB6010T, GB6015T, GB6016T, GB6019T, GB6024T, GB6027T |
| 4 | PTP-004 | GB1023T, GB6010T |
| 5 | PTP-005 | GB1023T, GB6010T, GB6027T |
| 6 | PTP-006 | GB1012T |
| 7 | PTP-007 | GB1023T, GB6010T, GB6027T |
| 8 | PTP-008 | NCH361T |
| 9 | PTP-009 | GB6003T |
| 10 | PTP-010 | GB6010T |
| 11 | CHI-001 | GB1002, GB1020T, GB1021T, GB1023T, GB1026T, GB6003T, GB6010T, GB6027T, |

Example 2: Expression Profiling of Genes Encoding the Peptides of the Invention

Not all peptides identified as presented on the surface of tumor cells by MHC molecules are suitable for immunotherapy, because the majority of these peptides are derived from normal cellular proteins expressed by many cell types. Only few of these peptides are tumor-associated and likely able to induce T cells with a high specificity of recognition for the tumor from which they were derived. To identify such peptides and minimize the risk for autoimmunity induced by vaccination, the inventors focused on those peptides that are derived from proteins that are over-expressed on tumor cells compared to the majority of normal tissues.

The ideal peptide is derived from a protein that is unique to the tumor and not present in any other tissue. To identify peptides that are derived from genes with an expression profile similar to the ideal, the identified peptides were assigned to the proteins and genes, respectively, from which they were derived and expression profiles of these genes were generated.

RNA Sources and Preparation

Surgically removed tissue specimens were provided by two different clinical sites (see Example 1) after written informed consent had been obtained from each patient.

Tumor tissue specimens were snap-frozen in liquid nitrogen immediately after surgery and later homogenized with mortar and pestle under liquid nitrogen. Total RNA was prepared from these samples using TRIzol (Invitrogen, Karlsruhe, Germany) followed by a cleanup with RNeasy (QIAGEN, Hilden, Germany); both methods were performed according to the manufacturer's protocol.

Total RNA from healthy human tissues was obtained commercially (Ambion, Huntingdon, UK; Clontech, Heidelberg, Germany; Stratagene, Amsterdam, Netherlands; BioChain, Hayward, Calif., USA). The RNA from several individuals (between 2 and 123 individuals) was mixed so that RNA from each individual was equally weighted. Leukocytes were isolated from blood samples of 4 healthy volunteers.

Quality and quantity of all RNA samples were assessed on an Agilent 2100 Bioanalyzer (Agilent, Waldbronn, Germany) using the RNA 6000 Pico LabChip Kit (Agilent).

Microarray Experiments

Gene expression analysis of all tumor and normal tissue RNA samples was performed by Affymetrix Human Genome (HG) U133A or HG-U133 Plus 2.0 oligonucleotide microarrays (Affymetrix, Santa Clara, Calif., USA). All steps were carried out according to the Affymetrix manual. Briefly, double-stranded cDNA was synthesized from 5-8 µg of total RNA, using SuperScript RTII (Invitrogen) and the oligo-dT-T7 primer (MWG Biotech, Ebersberg, Germany) as described in the manual. In vitro transcription was performed with the BioArray High Yield RNA Transcript Labelling Kit (ENZO Diagnostics, Inc., Farmingdale, N.Y., USA) for the U133A arrays or with the GeneChip IVT Labelling Kit (Affymetrix) for the U133 Plus 2.0 arrays, followed by cRNA fragmentation, hybridization, and staining with streptavidin-phycoerythrin and biotinylated anti-streptavidin antibody (Molecular Probes, Leiden, Netherlands). Images were scanned with the Agilent 2500A GeneArray Scanner (U133A) or the Affymetrix Gene-Chip Scanner 3000 (U133 Plus 2.0), and data were analysed with the GCOS software (Affymetrix), using default settings for all parameters. For normalisation, 100 housekeeping genes provided by Affymetrix were used. Relative expression values were calculated from the signal log ratios given by the software and the normal sample was arbitrarily set to 1.0.

Figure 2:
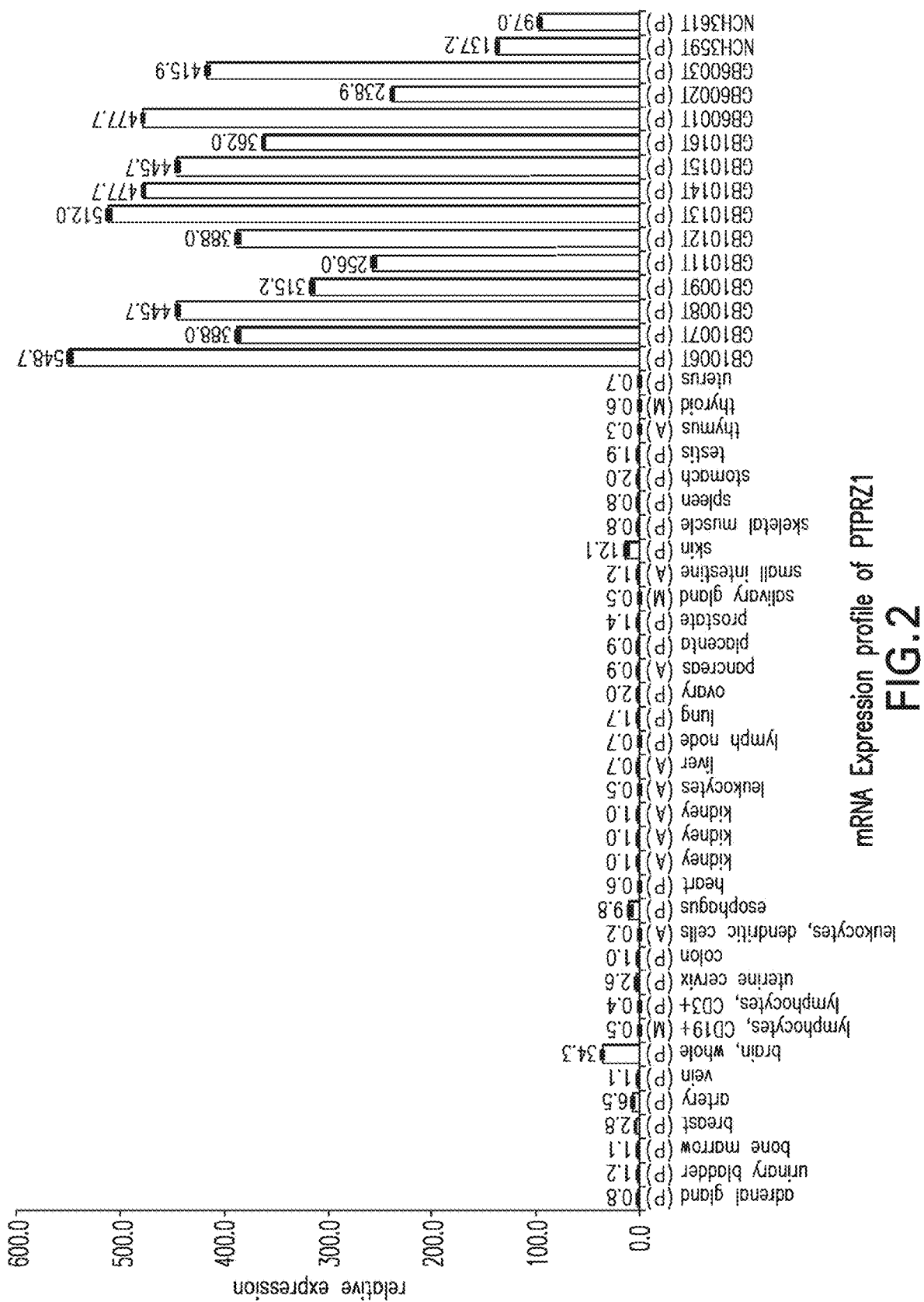
FIG. 2 depicts the mRNA expression profile of the gene PTPRZ1 encoding the glioblastoma associated peptides shown in Table 1. Expression of this gene is absent or very low in normal tissues while it is strongly increased in glioblastoma samples (GB 1006T to GB 1011 T; NCH359T and NCH361 T).
Figure 3A:
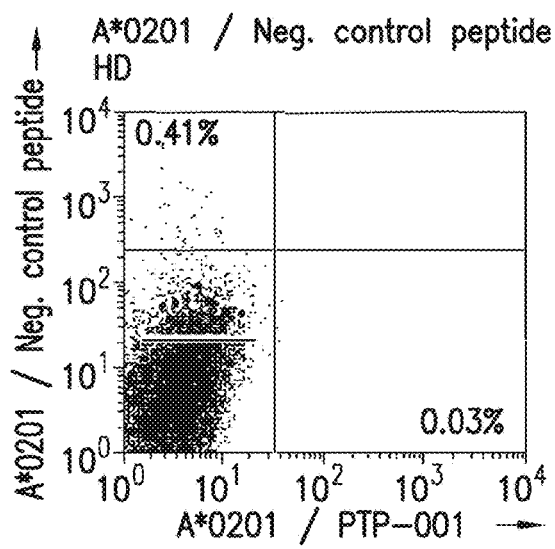
FIGS. 3A-3D show a representative example for PTP-002-specific CD8+ T cells in one healthy HLA-A *0201 donor following in vitro stimulation with PTP-002 as determined by flow cytometric analysis. CD8+ T cells were isolated from healthy donor human PBMCs and primed in vitro using molecularly defined "artificial antigen presenting cells" (aAPCs) loaded with co-stimulatory molecules and A*0201/PTP-002 (left diagram) or irrelevant A*0201 peptide (right diagram) (Walter et al., 2003). After three cycles of stimulation, the detection of peptide-reactive cells was performed by staining with PTP-002-plus irrelevant peptide tetramers. Cells were gated on CD8+ lymphocyte population and percentages represent the frequencies of tetramer-positive cells within this population.
Figure 3B:
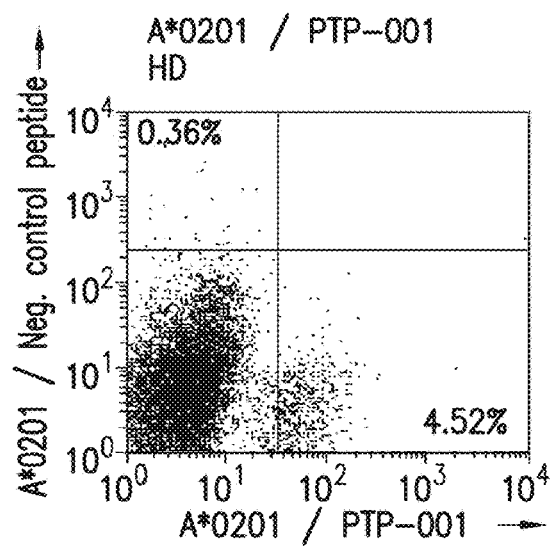
Figure 3C:
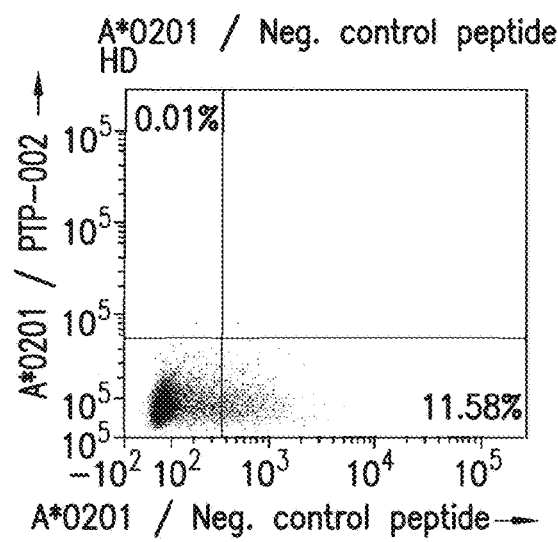
Figure 3D:
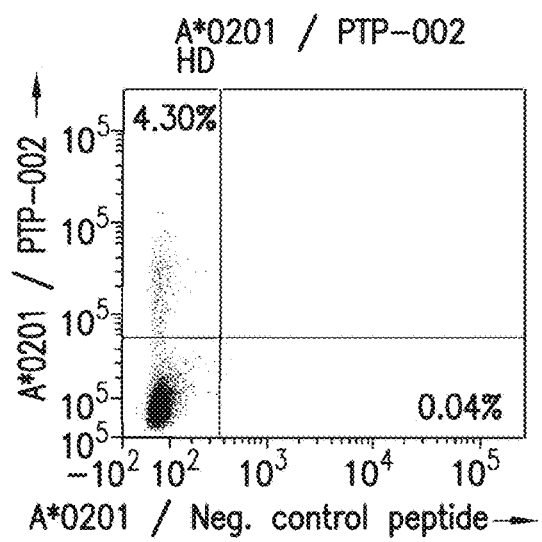

The expression profile of the source gene of all peptides of the present invention (PTPRZ 1) shows a high expression in glioblastoma tumor tissue whereas the gene is not expressed or expressed at very low levels in normal tissues FIG. 2).

Example 3: In Vitro Immunogenicity of MHC Class I Presented Peptides

In Vitro Priming of CD8+ T Cells

To perform in vitro stimulations by artificial antigen presenting cells (aAPC) loaded with peptide-MHC complex (pMHC) and anti-CD28 antibody, PBMCs (peripheral blood mononuclear cells) were isolated from fresh HLA-A*02+ buffy coats by using standard density gradient separation medium (PAA, Colbe, Germany). Buffy coats were obtained from the Katharinenhospital Stuttgart. Isolated PBMCs were incubated overnight in T-cell medium (TCM) for human in vitro priming consisting of RPMI-Glutamax (Invitrogen, Karlsruhe, Germany) supplemented with 10% heat inactivated human AB serum (PAA, Colbe, Germany), 100 U/ml Penicillin/100 µg/ml Streptomycin (Cambrex, Verviers, Belgium), 1 mM sodium pyruvate (CC Pro, Neustadt, Germany) and 20 µg/ml Gentamycin (Cambrex). CD8+ lymphocytes were isolated using the CD8+ MACS positive selection kit (Miltenyi, Bergisch Gladbach, Germany) according to the manufacturer's instructions. Obtained CD8+ T cells were incubated until use in TCM supplemented with 2.5 ng/ml IL-7 (PromoCell, Heidelberg, Germany) and 10 U/ml IL-2 (Chiron, Munich, Germany). Generation of pMHC/anti-CD28 coated beads, T-cell stimulations and readout was performed as described before (Walter et al., 2003) with minor modifications. Briefly, biotinylated recombinant HLA-A*0201 molecules lacking the transmembrane domain and biotinylated at the carboxy terminus of the heavy chain were produced following a method described by Altman et al., 1996). The purified costimulatory mouse IgG2a anti human CD28 Ab 9.3 (Jung et al., 1987) was chemically biotinylated using Sulfo-N-hydroxysuccinimidobiotin as recommended by the manufacturer (Perbio, Bonn, Germany). 5.60 µm large streptavidin coated polystyrene particles beads were used (Bangs Laboratories, Illinois/USA). pMHC was used as positive and negative controls were A*0201/MLA-001 (peptide ELAGIGILTV from modified Melan-A/MART-1) and A*0201/DDX5-001 (YLLPAIVHI from DDX5), respectively.

800,000 beads/200 µl were coated in 96-well plates in the presence of 600 ng biotin anti-CD28 plus 200 ng relevant biotin-pMHC (high density beads) or 2 ng relevant plus 200 ng irrelevant (pMHC library) MHC (low density beads). Stimulations were initiated in 96-well plates by conincubating 1×10$^6$ CD8+ T cells with 2×10$^5$ washed coated beads in 200 µl TCM supplemented with 5 ng/ml IL-12 (PromoCell) for 3-4 days at 37° C. Half of the medium was then exchanged by fresh TCM supplemented with 80 U/ml IL-2 and incubating was continued for 3-4 days at 37° C. This stimulation cycle was performed for a total of three times. Finally, tetrameric analyses were performed with fluorescent MHC tetramers (produced as described by (Altman et al., 1996)) plus antibody CD8-FITC clone SK1 (BD, Heidelberg, Germany) on a FACSCalibur or a LSR II flow cytometer (BD). Peptide specific cells were calculated as percentage of total CD8+ T cells. Evaluation of tetrameric analysis was performed using the software FCS Express (De Novo Software). In vitro priming of specific tetramer+ CD8+ lymphocytes was detected by appropriate gating and by comparing to negative control stimulations. Immunogenicity for a given antigen was detected if at least one evaluable in vitro stimulated well of one healthy donor was found to contain a specific CD8+ T-cell line after in vitro stimulation (i.e. this well contained at least 1% of specific tetramer+ among CD8+ T cells and the percentage of specific tetramer+ cells was at least 10× the median of the negative control stimulations).

A representative staining showing generation of T-cell lines specific for PTP-002 and PTP-001 is shown in FIGS. 3A-3D. The results are summarized in table 4 below.

TABLE 4

In vitro immunogenicity of peptides of the invention

| Antigen | Immunogenicity detected | Positive donors/ donors tested | Positive wells/ wells tested |
| --- | --- | --- | --- |
| PTP-001 | Yes | 6/6 (100%) | 33/96 (34%) |
| PTP-002 | Yes | 3/4 (75%) | 9/48 (19%) |
| PTP-003 | Yes | 2/4 (50%) | 8/48 (17%) |
| PTP-004 | Yes | 2/4 (50%) | 2/48 (4%) |
| PTP-005 | Yes | 4/4 (100%) | 25/48 (52%) |
| CHI-001 | Yes | 4/4 (100%) | 39/62 (63%) |

Results of in vitro immunogenicity experiments conducted by immatics and showing the percentage of positive tested donors and wells are summarized here. Results shown have been obtained by stimulation of CD8+ cells with high density beads. As different human serum lots may highly affect the immunogenicity results, only assays in which one and the same serum lot was used, were evaluated together.

Example 4: Binding of HLA Class I-Restricted Peptides to HLA-A*0201

The objective of this analysis was to evaluate the affinity of HLA class I peptides PTP-001, PTP-002, PTP-003, PTP-004, PTP-005 and CHI-001 to the MHC molecule coded by the HLA-A*0201 allele. Affinities for all peptides to HLA-A*0201 were comparable to the well-known control peptide HBV-001, dissociations constants ($K_D$) are in the range from 0.02 to 1.6 nM.

Principle of Test

Stable HLA/peptide complexes consist of three molecules: HLA heavy chain, beta-2 microglobulin (b2m) and the peptidic ligand. The activity of denatured recombinant HLA-A*0201 heavy chain molecules alone can be preserved making them functional equivalents of "empty HLA-A*0201 molecules." When diluted into aqueous buffer containing b2m and an appropriate peptide, these molecules fold rapidly and efficiently in an entirely peptide-dependent manner. The availability of these molecules is used in an ELISA-based assay to measure the affinity of interaction between peptide and HLA class I molecule (Sylvester-Hvid et al., 2002).

Purified recombinant HLA-A*0201 molecules were incubated together with b2m and graded doses of the peptide of interest. The amount of de novo-folded HLA/peptide complexes was determined by a quantitative ELISA. Dissociation constants ($K_D$ values) were calculated using a standard curve recorded from dilutions of a calibrant HLA/peptide complex.

Figure 4:
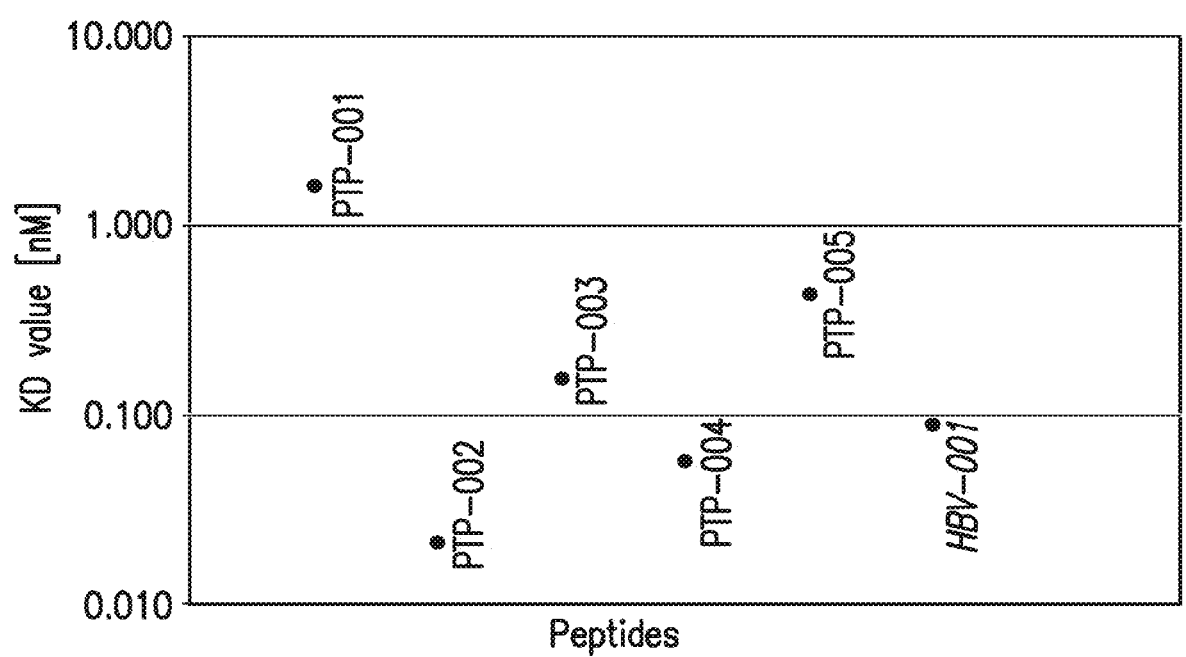
FIG. 4 shows the affinities of peptides of the invention to HLA-A*0201. Dissociation constants ($K_D$) of the HLA class I peptides and the viral marker peptide HBV-001 were measured by an ELISA-based assay (see Example 4).

Results are shown in FIG. 4. A lower $K_D$ value reflects higher affinity to HLA-A *0201. Affinities for all peptides to HLA-A*0201 were comparable to the well-known control peptide HBV-001, dissociations constants ($K_D$) are in the range from 0.02 to 1.6 nM.

REFERENCE LIST

Allison A C 1998; The mode of action of immunological adjuvants; Dev Biol Stand; 92:3-11.

Altman J D, Moss P A, Goulder P J, Barouch D H, Heyzer-Williams M G, Bell J I, McMichael A J, Davis M M (1996). Phenotypic analysis of antigen-specific T lymphocytes. Science 274, 94-96.

Appay V, Speiser D E, Rufer N, Reynard S, Barbey C, Cerottini J C, Leyvraz S, Pinilla C, Romero P (2006). Decreased specific CD8+ T cell cross-reactivity of antigen recognition following vaccination with Melan-A peptide. Eur. J Immunol. 36, 1805-1814.

Ariyama T, Hasegawa K, Inazawa J, Mizuno K, Ogimoto M, Katagiri T, Yakura H (1995). Assignment of the human protein tyrosine phosphatase, receptor-type, zeta (PT-PRZ) gene to chromosome band 7q31.3. Cytogenet. Cell Genet. 70, 52-54.

Barnea G, Silvennoinen O, Shaanan B, Honegger A M, Canoll P D, D'Eustachio P, Morse B, Levy J B, Laforgia S, Huebner K, (1993). Identification of a carbonic anhydrase-like domain in the extracellular region of RPTP gamma defines a new subfamily of receptor tyrosine phosphatases. Mol. Cell Biol. 13, 1497-1506.

Boyton R J, Lohmann T, Londei M, Kalbacher H, Halder T, Frater A J, Douek D C, Leslie D G, Flavell R A, Altmann D M (1998). Glutamic acid decarboxylase T lymphocyte responses associated with susceptibility or resistance to type I diabetes: analysis in disease discordant human twins, non-obese diabetic mice and HLA-DQ transgenic mice. Int. Immunol. 10, 1765-1776.

Bruckdorfer T, Marder O, Albericio F. (2004) From production of peptides in milligram amounts for research to multi-ton quantities for drugs of the future Curr Pharm Biotechnol. February; 5(1):29-43.

Brunsvig P F, Aamdal S, Gjertsen M K, Kvalheim G, Markowski-Grimsrud C J, Sve I, Dyrhaug M, Trachsel S, Møller M, Eriksen J A, Gaudernack G (2006); Telomerase peptide vaccination: a phase I/II study in patients with non-small cell lung cancer; Cancer Immunol Immunother; 55(12):1553-1564.

Burton E C, Prados M D (2000). Malignant gliomas. Curr. Treat. Options. Oncol 1, 459-468.

CBTRUS. Primary Brain Tumors in the United States, Statistical Report. 2006.

Ref Type: Internet Communication.

Cheever M A, Chen W, Disis M L, Takahashi M, Peace D J (1993). T-cell immunity to oncogenic proteins including mutated ras and chimeric bcr-abl. Ann N. Y. Acad. Sci. 690, 101-112.

Colombetti S, Basso V, Mueller D L, Mondino A (2006). Prolonged TCR/CD28 engagement drives IL-2-independent T cell clonal expansion through signaling mediated by the mammalian target of rapamycin. J Immunol. 176, 2730-2738.

Cresswell P (1994). Assembly, transport, and function of MHC class II molecules. Annu. Rev. Immunol. 12, 259-293.

Dazzi C, Cariello A, Giannini M, Del D M, Giovanis P, Fiorentini G, Leoni M, Rosti G, Turci D, Tienghi A, Vertogen B, Zumaglini F, De G U, Marangolo M (2000). A sequential chemo-radiotherapeutic treatment for patients with malignant gliomas: a phase II pilot study. Anticancer Res. 20, 515-518.

Dengjel J, Nastke M D, Gouttefangeas C, Gitsioudis G, Schoor O, Altenberend F, Muller M, Kramer B, Missiou A, Sauter M, Hennenlotter J, Wernet D, Stenzl A, Rammensee H G, Klingel K, Stevanovic S (2006). Unexpected Abundance of HLA Class II Presented Peptides in Primary Renal Cell Carcinomas. Clin Cancer Res. 12, 4163-4170.

Dix A R, Brooks W H, Roszman T L, Morford L A (1999). Immune defects observed in patients with primary malignant brain tumors. J Neuroimmunol. 100, 216-232.

Dudley M E, Wunderlich J R, Robbins P F, Yang J C, Hwu P, Schwartzentruber D J, Topalian S L, Sherry R, Restifo N P, Hubicki A M, Robinson M R, Raffeld M, Duray P, Seipp C A, Rogers-Freezer L, Morton K E, Mavroukakis S A, White D E, Rosenberg S A (2002). Cancer regression and autoimmunity in patients after clonal repopulation with antitumor lymphocytes. Science 298, 850-854.

Dudley M E, Wunderlich J R, Yang J C, Sherry R M, Topalian S L, Restifo N P, Royal R E, Kammula U, White D E, Mavroukakis S A, Rogers L J, Gracia G J, Jones S A, Mangiameli D P, Pelletier M M, Gea-Banacloche J, Robinson M R, Berman D M, Filie A C, Abati A, Rosenberg S A (2005). Adoptive cell transfer therapy following non-myeloablative but lymphodepleting chemotherapy for the treatment of patients with refractory metastatic melanoma. J. Clin. Oncol. 23, 2346-2357.

Dupuis M, Murphy T J, Higgins D, Ugozzoli M, van Nest G, Ott G, McDonald D M (1998); Dendritic cells internalize vaccine adjuvant after intramuscular injection; Cell Immunol; 186(1):18-27.

Falk, K., Rotzschke, O., Stevanovic, S., Jung, G. & Rammensee, H. G. Allele-specific motifs revealed by sequencing of self-peptides eluted from MHC molecules. Nature 351, 290-296 (1991).

Fong L, Brockstedt D, Benike C, Wu L, Engleman E G (2001a). Dendritic cells injected via different routes induce immunity in cancer patients. J. Immunol. 166, 4254-4259.

Fong L, Hou Y, Rivas A, Benike C, Yuen A, Fisher G A, Davis M M, Engleman E G (2001b). Altered peptide ligand vaccination with Flt3 ligand expanded dendritic cells for tumor immunotherapy. Proc. Natl. Acad. Sci. U.S. A 98, 8809-8814.

Gabrilovich D I, Cunningham H T, Carbone D P; IL-12 and mutant P53 peptide-pulsed dendritic cells for the specific immunotherapy of cancer; J Immunother Emphasis Tumor Immunol. 1996 (6):414-418.

Galon J, Costes A, Sanchez-Cabo F, Kirilovsky A, Mlecnik B, Lagorce-Pages C, Tosolini M, Camus M, Berger A, Wind P, Zinzindohoue F, Bruneval P, Cugnenc P H, Trajanoski Z, Fridman W H, Pages F (2006). Type, density, and location of immune cells within human colorectal tumors predict clinical outcome. Science 313, 1960-1964.

Gattinoni L, Powell D J, Jr., Rosenberg S A, Restifo N P (2006). Adoptive immunotherapy for cancer: building on success. Nat. Rev. Immunol. 6, 383-393.

Gebbink M F, van E, I, Hateboer G, Suijkerbuijk R, Beijersbergen R L, Geurts van KA, Moolenaar W H (1991). Cloning, expression and chromosomal localization of a new putative receptor-like protein tyrosine phosphatase. FEBS Lett. 290, 123-130.

Gnjatic S, Atanackovic D, Jager E, Matsuo M, Selvakumar A, Altorki N K, Maki R G, Dupont B, Ritter G, Chen Y T, Knuth A, Old L J (2003). Survey of naturally occurring CD4+ T cell responses against NY-ESO-1 in cancer patients: correlation with antibody responses. Proc Natl. Acad. Sci. U. S. A 100, 8862-8867.

Hammer J, Gallazzi F, Bono E, Karr R W, Guenot J, Valsasnini P, Nagy Z A, Sinigaglia F (1995). Peptide binding specificity of HLA-DR4 molecules: correlation with rheumatoid arthritis association. J Exp. Med 181, 1847-1855.

Hanada K, Yewdell J W, Yang J C (2004). Immune recognition of a human renal cancer antigen through post-translational protein splicing. Nature 427, 252-256.

Harroch S, Furtado G C, Brueck W, Rosenbluth J, Lafaille J, Chao M, Buxbaum J D, Schlessinger J (2002). A critical role for the protein tyrosine phosphatase receptor type Z in functional recovery from demyelinating lesions. Nat. Genet. 32, 411-414.

Heimberger A B, Hussain S F, Aldape K, Sawaya R, Archer G A, Friedman H, Reardon D, Friedman A, Bigner D D, Sampson J H. Tumor-specific peptide vaccination in newly-diagnosed patients with GBM. Journal of Clinical Oncology, 2006 ASCO Annual Meeting Proceedings Part I Vol 24, No. 18S (June 20 Supplement), 2006: 2529. 6-20-2006.

Hill et al. (1995) J. Exp. Med. 181, 2221-2228.

Jerome et al. (1993) J. Immunol. 151, 1654-1662.

Jochmus et al. (1997) J. Gen. Virol. 78, 1689-1695.

Jung G, Ledbetter J A, Muller-Eberhard H J (1987). Induction of cytotoxicity in resting human T lymphocytes bound to tumor cells by antibody heteroconjugates. Proc Natl Acad Sci USA 84, 4611-4615.

Kaplan R, Morse B, Huebner K, Croce C, Howk R, Ravera M, Ricca G, Jaye M, Schlessinger J (1990). Cloning of three human tyrosine phosphatases reveals a multigene family of receptor-linked protein-tyrosine-phosphatases expressed in brain. Proc Natl. Acad. Sci. U. S. A 87, 7000-7004.

Karre and Ljunggren (1985) J. Exp. Med. 162, 1745.

Kawakami et al. (1992) J. Immunol. 148, 638-643.

Kennedy R C, Shearer M H, Watts A M, Bright R K (2003). CD4+T lymphocytes play a critical role in antibody production and tumor immunity against simian virus 40 large tumor antigen. Cancer Res. 63, 1040-1045.

Kobayashi H, Omiya R, Ruiz M, Huarte E, Sarobe P, Lasarte J J, Herraiz M, Sangro B, Prieto J, Borras-Cuesta F, Celis E (2002). Identification of an antigenic epitope for helper T lymphocytes from carcinoembryonic antigen. Clin Cancer Res. 8, 3219-3225.

Arthur M. Krieg, Therapeutic potential of Toll-like receptor 9 activation 2006, Nature Reviews, Drug Discovery, 5, JUNE, 471-484.

Krueger N X, Streuli M, Saito H (1990). Structural diversity and evolution of human receptor-like protein tyrosine phosphatases. EMBO J 9, 3241-3252.

Lemmel C, Weik S, Eberle U, Dengjel J, Kratt T, Becker H D, Rammensee H G, Stevanovic S (2004). Differential quantitative analysis of MHC ligands by mass spectrometry using stable isotope labeling. Nat. Biotechnol. 22, 450-454.

Levy J B, Canoll P D, Silvennoinen O, Barnea G, Morse B, Honegger A M, Huang J T, Cannizzaro L A, Park S H, Druck T, (1993). The cloning of a receptor-type protein tyrosine phosphatase expressed in the central nervous system. J Biol. Chem. 268, 10573-10581.

Longenecker et al. (1993) Ann. NY Acad. Sci. 690, 276-291.

Lu et al. (1981) J. Org. Chem. 46, 3433.

Lu K V, Jong K A, Kim G Y, Singh J, Dia E Q, Yoshimoto K, Wang M Y, Cloughesy T F, Nelson S F, Mischel P S (2005). Differential induction of glioblastoma migration and growth by two forms of pleiotrophin. J Biol Chem. 280, 26953-26964.

Macdonald D R (2001). Temozolomide for recurrent high-grade glioma. Semin. Oncol 28, 3-12.

Mach B, Steimle V, Martinez-Soria E, Reith W (1996). Regulation of MHC class II genes: lessons from a disease. Annu. Rev. Immunol. 14, 301-331.

A Mahdavi and BJ Monk Recent advances in human papillomavirus vaccines Curr Oncol Rep 2006, 6, 465-472.

Malcherek G, Gnau V, Stevanovic S, Rammensee H G, Jung G, Melms A (1994). Analysis of allele-specific contact sites of natural HLA-DR17 ligands. J Immunol. 153, 1141-1149.

Manici S, Sturniolo T, Imro M A, Hammer J, Sinigaglia F, Noppen C, Spagnoli G, Mazzi B, Bellone M, Dellabona P, Protti M P (1999). Melanoma cells present a MAGE-3 epitope to CD4(+) cytotoxic T cells in association with histocompatibility leukocyte antigen DR11. J Exp. Med 189, 871-876.

Morgan R A, Dudley M E, Wunderlich J R, Hughes M S, Yang J C, Sherry R M, Royal R E, Topalian S L, Kammula U S, Restifo N P, Zheng Z, Nahvi A, de Vries C R, Rogers-Freezer L J, Mavroukakis SA, Rosenberg S A (2006). Cancer Regression in Patients After Transfer of Genetically Engineered Lymphocytes. Science.

Mulholland P J, Fiegler H, Mazzanti C, Gorman P, Sasieni P, Adams J, Jones T A, Babbage J W, Vatcheva R, Ichimura K, East P, Poullikas C, Collins V P, Carter N P, Tomlinson I P, Sheer D (2006). Genomic profiling identifies discrete deletions associated with translocations in glioblastoma multiforme. Cell Cycle 5, 783-791.

Strubin, M., Mach, B. and Long, E. G. (1984) The complete sequence of the mRNA for the HLA-DR-associated invariant chain reveals a polypeptide with an unusual transmembrane polarity EMBO J. 3 (4), 869-872.

Napolitano M, Keime-Guibert F, Monjour A, Lafitte C, Ameri A, Cornu P, Broet P, Delattre J Y (1999). Treatment of supratentorial glioblastoma multiforme with radiotherapy and a combination of BCNU and tamoxifen: a phase II study. J Neurooncol. 45, 229-235.

Nieder C, Grosu A L, Molls M (2000). A comparison of treatment results for recurrent malignant gliomas. Cancer Treat. Rev. 26, 397-409.

Novellino L, Castelli C, Parmiani G (2005). A listing of human tumor antigens recognized by T cells: March 2004 update. Cancer Immunol. Immunother. 54, 187-207.

Pascolo S. 2006: Vaccination with messenger RNA Methods Mol Med, 127; 23-40.

Peoples et al. (1995) Proc. Natl. Acad. Sci. USA 92, 432-436.

Perez-Pinera P, Garcia-Suarez O, Menendez-Rodriguez P, Mortimer J, Chang Y, Astudillo A, Deuel T F (2007). The receptor protein tyrosine phosphatase (RPTP)beta/zeta is expressed in different subtypes of human breast cancer. Biochem. Biophys. Res. Commun. 362, 5-10.

Plebanski et al. (1995) Eur. J. Immunol. 25, 1783-1787.

Porta et al. (1994) Virology 202, 449-955.

Prados M D, Levin V (2000). Biology and treatment of malignant glioma. Semin. Oncol 27, 1-10.

Qin Z, Blankenstein T (2000). CD4+ T cell—mediated tumor rejection involves inhibition of angiogenesis that is dependent on IFN gamma receptor expression by nonhematopoietic cells. Immunity. 12, 677-686.

Qin Z, Schwartzkopff J, Pradera F, Kammertoens T, Seliger B, Pircher H, Blankenstein T (2003). A critical requirement of interferon gamma-mediated angiostasis for tumor rejection by CD8+ T cells. Cancer Res. 63, 4095-4100.

Rammensee H G, Bachmann J, Emmerich N P, Bachor O A, Stevanovic S (1999). SYFPEITHI: database for MHC ligands and peptide motifs. Immunogenetics 50, 213-219.

Rammensee, H. G., Bachmann, J., and Stevanovic, S. (1997). MHC Ligands and Peptide Motifs. Springer-Verlag, Heidelberg, Germany).

Recklies A D, White C, Ling H; The chitinase 3-like protein human cartilage glycoprotein 39 (HC-gp39) stimulates proliferation of human connective-tissue cells and activates both extracellular signal-regulated kinase- and protein kinase B-mediated signalling pathways; Biochem J. 2002; 365:119-126.

Rini B I, Weinberg V, Fong L, Conry S, Hershberg R M, Small E J (2006); Combination immunotherapy with prostatic acid phosphatase pulsed antigen-presenting cells (Provenge) plus bevacizumab in patients with serologic progression of prostate cancer after definitive local therapy; Cancer; 107(1):67-74).

Rosenberg S A, Lotze M T, Muul L M, Chang A E, Avis F P, Leitman S, Linehan W M, Robertson C N, Lee R E, Rubin J T (1987). A progress report on the treatment of 157 patients with advanced cancer using lymphokine-activated killer cells and interleukin-2 or high-dose interleukin-2 alone. N. Engl. J. Med. 316, 889-897.

Rosenberg S A, Packard B S, Aebersold P M, Solomon D, Topalian S L, Toy S T, Simon P, Lotze M T, Yang J C, Seipp C A. (1988). Use of tumor-infiltrating lymphocytes and interleukin-2 in the immunotherapy of patients with metastatic melanoma. A preliminary report. N. Engl. J Med 319, 1676-1680.

Roth W, Weller M (1999). Chemotherapy and immunotherapy of malignant glioma: molecular mechanisms and clinical perspectives. Cell Mol. Life Sci. 56, 481-506.

Sablotzki A, Ebel H, Muhling J, Dehne M G, Nopens H, Giesselmann H, Hempelmann G (2000). Dysregulation of immune response following neurosurgical operations. Acta Anaesthesiol. Scand. 44, 82-87.

Saiki et al. (1988) Science 239, 487-491.

Small E J, Schellhammer P F, Higano C S, Redfern C H, Nemunaitis J J, Valone F H, Verjee S S, Jones L A, Hershberg R M. (2006); Placebo-controlled phase 3 trial of immunologic therapy with sipuleucel-T (APC8015) in patients with metastatic, asymptomatic hormone refractory prostate cancer; J Clin Oncol; 24(19):3089-3094.

Schubert U, Anton L C, Gibbs J, Norbury C C, Yewdell J W, Bennink J R (2000). Rapid degradation of a large fraction of newly synthesized proteins by proteasomes. Nature 404, 770-774.

Seeger, F. H. et al. 1999 The HLA-A*6601 peptide motif: prediction by pocket structure and verification by peptide analysis. Immunogenetics 49, 571-576.

Shedlock D J, Shen H (2003). Requirement for CD4 T cell help in generating functional CD8 T cell memory. Science 300, 337-339.

Singh-Jasuja H, Emmerich N P, Rammensee H G (2004). The Tubingen approach: identification, selection, and validation of tumor-associated HLA peptides for cancer therapy. Cancer Immunol. Immunother. 53, 187-195.

M. Staehler, A. Stenzl, P. Y. Dietrich, T. Eisen, A. Haferkamp, J. Beck, A. Mayer, S. Walter, H. Singh, J. Frisch, C. G. Stief (2008); An open label study to evaluate the safety and immunogenicity of the peptide based cancer vaccine IMA901, ASCO meeting 2007; Abstract No 3017.

R. Stan, J D Wolchok and A D Cohen DNA vaccines against cancer Hematol Oncol Clin North Am 2006, 3; 613-636.

Sun J C, Bevan M J (2003). Defective CD8 T cell memory following acute infection without CD4 T cell help. Science 300, 339-342.

Sylvester-Hvid C, Kristensen N, Blicher T, Ferre H, Lauemoller S L, Wolf X A, Lamberth K, Nissen M H, Pedersen L O, Buus S (2002). Establishment of a quantitative ELISA capable of determining peptide—MHC class I interaction. Tissue Antigens 59, 251-258.

(Takaishi S, Wang T C; Gene expression profiling in a mouse model of Helicobacter-induced gastric cancer; Cancer Sci. 2007 (3): 284-293).

Tompkins S M, Rota P A, Moore J C, Jensen P E (1993). A europium fluoroimmunoassay for measuring binding of antigen to class II MHC glycoproteins. J Immunol. Methods 163, 209-216.

van der Bruggen P, Traversari C, Chomez P, Lurquin C, De P E, Van den EB, Knuth A, Boon T (1991). A gene encoding an antigen recognized by cytolytic T lymphocytes on a human melanoma. Science 254, 1643-1647.

Vigneron N, Stroobant V, Chapiro J, Ooms A, Degiovanni G, Morel S, van der BP, Boon T, Van Den Eynde B J (2004). An antigenic peptide produced by peptide splicing in the proteasome. Science 304, 587-590.

Vogt A B, Kropshofer H, Kalbacher H, Kalbus M, Rammensee H G, Coligan J E, Martin R (1994). Ligand motifs of HLA-DRB5*0101 and DRB1*1501 molecules delineated from self-peptides. J. Immunol. 153, 1665-1673.

Walter S, Herrgen L, Schoor O, Jung G, Wernet D, Buhring H J, Rammensee H G, Stevanovic S (2003). Cutting edge: predetermined avidity of human CD8 T cells expanded on calibrated MHC/anti-CD28-coated microspheres. J. Immunol. 171, 4974-4978.

Wang J C, Livingstone A M (2003). Cutting edge: CD4+ T cell help can be essential for primary CD8+ T cell responses in vivo. J Immunol. 171, 6339-6343.

Wang V, Davis D A, Haque M, Huang L E, Yarchoan R (2005). Differential gene up-regulation by hypoxia-inducible factor-1alpha and hypoxia-inducible factor-2alpha in HEK293T cells. Cancer Res. 65, 3299-3306.

Weinschenk T, Gouttefangeas C, Schirle M, Obermayr F, Walter S, Schoor O, Kurek R, Loeser W, Bichler K H, Wernet D, Stevanovic S, Rammensee H G (2002). Integrated functional genomics approach for the design of patient-individual antitumor vaccines. Cancer Res. 62, 5818-5827.

Wu C W, Li A F, Chi C W, Lin W C (2006). Protein tyrosine-phosphatase expression profiling in gastric cancer tissues. Cancer Lett. 242, 95-103.

Yee C, Thompson J A, Byrd D, Riddell S R, Roche P, Celis E, Greenberg P D (2002). Adoptive T cell therapy using antigen-specific CD8+ T cell clones for the treatment of patients with metastatic melanoma: in vivo persistence, migration, and antitumor effect of transferred T cells. Proc. Natl. Acad. Sci. U. S. A 99, 16168-16173.

Zaremba S, Barzaga E, Zhu M, Soares N, Tsang K Y, Schlom J (1997). Identification of an enhancer agonist cytotoxic T lymphocyte peptide from human carcinoembryonic antigen. Cancer Res. 57, 4570-4577.

Zeh H J, III, Perry-Lalley D, Dudley M E, Rosenberg S A, Yang J C (1999). High avidity CTLs for two self-antigens demonstrate superior in vitro and in vivo antitumor efficacy. J Immunol. 162, 989-994.

The invention claimed is:

1. A peptide consisting of the amino acid sequence of AIIDGVESV (SEQ ID NO: 3) in the form of a pharmaceutically acceptable salt.

2. The peptide according to claim 1, wherein the pharmaceutically acceptable salt is a chloride salt, acetate salt, or trifluoroacetate salt.

3. The peptide of claim 2, wherein the pharmaceutically acceptable salt is the trifluoroacetate salt.

4. The peptide of claim 2, wherein the pharmaceutically acceptable salt is the chloride salt.

5. The peptide of claim 2, wherein the pharmaceutically acceptable salt is the acetate salt.

6. The peptide according to claim 1, wherein the peptide is conjugated with a suitable carrier.

7. The peptide according to claim 6, wherein the suitable carrier is keyhole limpet haemocyanin or mannan.

8. A pharmaceutical composition comprising the peptide of claim 1 and an immune-enhancing amount of an adjuvant.

9. The pharmaceutical composition of claim 8, wherein the adjuvant is at least one selected from the group consisting of anti-CD40 antibody, imiquimod, resiquimod, GM-CSF, cyclophosphamide, sunitinib, bevacizumab, interferon-alpha, interferon-beta, CpG oligonucleotides and derivatives, poly-(I:C) and derivatives, RNA, sildenafil, particulate formulations with poly(lactide co-glycolide) (PLG), virosomes, interleukin (IL)-1, IL-2, IL-4, IL-7, IL-12, IL-13, IL-15, IL-21, and IL-23.

10. The pharmaceutical composition according to claim 9, wherein the adjuvant comprises IL-1.

11. The pharmaceutical composition according to claim 9, wherein the adjuvant comprises IL-2.

12. The pharmaceutical composition according to claim 9, wherein the adjuvant comprises IL-4.

13. The pharmaceutical composition according to claim 9, wherein the adjuvant comprises IL-7.

14. The pharmaceutical composition according to claim 9, wherein the adjuvant comprises IL-12.

15. The pharmaceutical composition according to claim 9, wherein the adjuvant comprises IL-13.

16. The pharmaceutical composition according to claim 9, wherein the adjuvant comprises IL-15.

17. The pharmaceutical composition according to claim 9, wherein the adjuvant comprises IL-21.

18. The pharmaceutical composition according to claim 9, wherein the adjuvant comprises IL-23.

19. The peptide in the form of a pharmaceutically acceptable salt of claim 1, wherein said peptide is produced by solid phase peptide synthesis or produced by a yeast cell or bacterial cell expression system.

20. A composition comprising the peptide of claim 1, wherein the composition is a pharmaceutical composition and comprises water and a buffer.

\* \* \* \* \*

SEQUENCE LISTING

```
<160> NUMBER OF SEQ ID NOS: 11

<210> SEQ ID NO 1
<211> LENGTH: 9
<212> TYPE: PRT
<213> ORGANISM: Homo sapiens

<400> SEQUENCE: 1

Ala Leu Thr Thr Leu Met His Gln Leu
1               5

<210> SEQ ID NO 2
<211> LENGTH: 9
<212> TYPE: PRT
<213> ORGANISM: Homo sapiens

<400> SEQUENCE: 2

Phe Leu Tyr Lys Val Ile Leu Ser Leu
1               5

<210> SEQ ID NO 3
<211> LENGTH: 9
<212> TYPE: PRT
<213> ORGANISM: Homo sapiens

<400> SEQUENCE: 3

Ala Ile Ile Asp Gly Val Glu Ser Val
1               5

<210> SEQ ID NO 4
<211> LENGTH: 9
<212> TYPE: PRT
<213> ORGANISM: Homo sapiens

<400> SEQUENCE: 4

Phe Leu Leu Pro Asp Thr Asp Gly Leu
1               5

<210> SEQ ID NO 5
<211> LENGTH: 9
<212> TYPE: PRT
<213> ORGANISM: Homo sapiens

<400> SEQUENCE: 5

Lys Val Phe Ala Gly Ile Pro Thr Val
1               5

<210> SEQ ID NO 6
<211> LENGTH: 9
<212> TYPE: PRT
<213> ORGANISM: Homo sapiens
```

```
<400> SEQUENCE: 6

Gln Gln Ser Asp Tyr Ser Ala Ala Leu
1               5

<210> SEQ ID NO 7
<211> LENGTH: 9
<212> TYPE: PRT
<213> ORGANISM: Homo sapiens

<400> SEQUENCE: 7

Thr Gln Asp Asp Tyr Val Leu Glu Val
1               5

<210> SEQ ID NO 8
<211> LENGTH: 9
<212> TYPE: PRT
<213> ORGANISM: Homo sapiens

<400> SEQUENCE: 8

Gln His Glu Gly Thr Val Asn Ile Phe
1               5

<210> SEQ ID NO 9
<211> LENGTH: 12
<212> TYPE: PRT
<213> ORGANISM: Homo sapiens

<400> SEQUENCE: 9

Ser Val Phe Gly Asp Asp Asn Lys Ala Leu Ser Lys
1               5                   10

<210> SEQ ID NO 10
<211> LENGTH: 14
<212> TYPE: PRT
<213> ORGANISM: Homo sapiens

<400> SEQUENCE: 10

Glu Ile Gly Trp Ser Tyr Thr Gly Ala Leu Asn Gln Lys Asn
1               5                   10

<210> SEQ ID NO 11
<211> LENGTH: 9
<212> TYPE: PRT
<213> ORGANISM: Homo sapiens

<400> SEQUENCE: 11

Ser Leu Trp Ala Gly Val Val Val Leu
1               5
```